US007763451B2

(12) United States Patent
Shiloach et al.

(10) Patent No.: US 7,763,451 B2
(45) Date of Patent: Jul. 27, 2010

(54) **METHODS FOR PREPARING *BACILLUS ANTHRACIS* PROTECTIVE ANTIGEN FOR USE IN VACCINES**

(75) Inventors: Joseph Shiloach, Rockville, MD (US); Stephen H. Leppla, Bethesda, MD (US); Delia M. Ramirez, Bethesda, MD (US); Rachel Schneerson, Bethesda, MD (US); John B. Robbins, Chevy Chase, MD (US); S. Dana Hsu, Bethesda, MD (US); Mary Jo Rosovitz, Germantown, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1523 days.

(21) Appl. No.: 10/290,712

(22) Filed: Nov. 8, 2002

(65) Prior Publication Data

US 2004/0076638 A1    Apr. 22, 2004

Related U.S. Application Data

(60) Provisional application No. 60/344,505, filed on Nov. 9, 2001.

(51) Int. Cl.
*C12N 1/00* (2006.01)
*C12N 1/20* (2006.01)
*C12P 1/00* (2006.01)
*A61K 39/38* (2006.01)
*A61K 39/02* (2006.01)
*A61K 39/07* (2006.01)

(52) U.S. Cl. ................... 435/243; 435/41; 435/252.31; 424/184.1; 424/236.1; 424/246.1

(58) Field of Classification Search ............... 435/71.1, 435/69.1, 320.1; 424/184.1, 234.1; 514/2
See application file for complete search history.

(56) References Cited

U.S. PATENT DOCUMENTS

| | | | |
|---|---|---|---|
| 3,710,795 A | | 1/1973 | Higuchi et al. |
| 4,038,142 A | * | 7/1977 | Turcotte et al. .......... 435/253.1 |
| 5,210,035 A | | 5/1993 | Stocker |
| 5,591,631 A | | 1/1997 | Leppla et al. |
| 5,677,274 A | | 10/1997 | Leppla et al. |
| 5,747,309 A | | 5/1998 | Allan et al. |
| 5,840,312 A | | 11/1998 | Mock et al. |
| 6,267,966 B1 | * | 7/2001 | Baillie ..................... 424/200.1 |
| 6,316,006 B1 | | 11/2001 | Worsham et al. |
| 6,387,665 B1 | * | 5/2002 | Ivins et al. ................. 435/71.1 |

FOREIGN PATENT DOCUMENTS

WO    WO 01/21656 A2    3/2001

WO    WO 01/82788 A2    11/2001

OTHER PUBLICATIONS

Farchaus et al (Applied and Environmental Microbiology, Mar. 1998, p. 982-991, vol. 64, No. 3).*
Thomas E. Creighton, in his book, "Proteins: Structures and Molecular Properties, 1984", (pp. 314-315).*
Thomas E. Creighton, in his book "Protein Structure: A Practical Approach, 1989; pp. 184-186".*
Nosoh, Y. et al in "Protein Stability and Stabilization through Protein Engineering, 1991" (chapter 7, p. 197, second paragraph).*
Singh et al (The Journal of Biological Chemistry, vol. 269, No. 46, p. 29039-29046, 1994).*
Glick et al (Molecular Biotechnology, Principles and Applications of Recombinant DNA, American Society for Microbiology, 1994).*
Farchaus et al (Applied and Environmental Microbiology, Mar. 1998, p. 982-991, vol. 64, No. 3).*
De Veth (J. Dairy Sci, 84:1449-1457).*
Bowie et al (Science, 1990, 257:1306-1310).*
Farchaus et al (Applied and Environmental Microbiology, Mar. 1998, p. 982-991, vol. 64, No. 3).*
Gupta et al (Biochemical and Biophysical Research Communications 285, Jul. 2001,1025-1033).*
Ahuja et al., "Rapid purification of recombinant anthrax-protective antigen under nondenaturing conditions," *Biochem. Biophys. Res. Commun.* 286:6-11, 2001.
Baillie et al., "The expression of the protective antigen of *Bacillus anthracis* in *Bacillus subtilis*," *J. Appl. Microbiol.* 84:741-746, 1998.
Bartkus et al., "Transcriptional regulation of the protective antigen gene of *Bacillus anthracis*," *Infect. Immun.* 57:2295-2300, 1989.
Chase, H.A., "Purification of proteins by adsorption chromatography in expanded beds," *Trends Biotechnol.* 12:296-303, 1994.
Chauhan et al., "Constitutive expression of protective antigen gene of *Bacillus anthracis* in *Escherichia coli*," *Biochem. Biophys. Res. Commun.* 283:308-315, 2001.
Chu et al., "Preparation, characterization, and immunogenicity of conjugates composed of the O-specific polysaccharide of *Shigella dysenteriae* type 1 (Shiga's Bacillus) bound to tetanus toxoid," *Infect. Immun.* 59:4450-4458, 1991.
Coulson et al., "*Bacillus anthracis* protective antigen, expressed in *Salmonella typhimurium* SL 3261, affords protection against anthrax spore challenge," *Vaccine* 12:1395-1401, 1994.
Ezzell and Welkos, "The capsule of *Bacillus anthracis*, a review," *J. Appl. Microbiol.* 87:250, 1999.

(Continued)

*Primary Examiner*—Vanessa L. Ford
(74) *Attorney, Agent, or Firm*—Klarquist Sparkman, LLP

(57) ABSTRACT

The invention relates to improved methods of producing and recovering *B. anthracis* protective antigen (PA), especially modified PA which is protease resistant, and to methods of using of these PAs or nucleic acids encoding these PAs for eliciting an immunogenic response in humans, including responses which provide protection against, or reduce the severity of, *B. anthracis* bacterial infections and which are useful to prevent and/or treat illnesses caused by *B. anthracis*, such as inhalation anthrax, cutaneous anthrax and gastrointestinal anthrax.

30 Claims, 4 Drawing Sheets

OTHER PUBLICATIONS

Farchaus et al., "Purification and characterization of the major surface array protein from the avirulent *Bacillus anthracis* Delta Sterne-1," *J. Bacteriol.* 177:2481-2489, 1995.

Farchaus et al., "Fermentation, purification, and characterization of protective antigen from a recombinant, avirulent strain of *Bacillus anthracis*," *Appl. Environ. Microbiol.* 64:982-991, 1998.

Fellows et al., "Efficacy of a human anthrax vaccine in guinea pigs, rabbits, and rhesus macaques against challenge by *Bacillus anthracis* isolates of diverse geographical origin," *Vaccine* 19:3241-3247, 2001.

Fouet et al., "*Bacillus anthracis* surface: capsule and S-layer," *J. Appl. Microbiol.* 87:251-255, 1999.

Gladstone, "Immunity to anthrax: protective antigen present in cell-free culture filtrates," *Br. J. Exp. Pathol.* 27:394-418, 1946.

Gupta et al., "Expression and purification of the recombinant protective antigen of *Bacillus anthracis*," *Protein Expr. Purif.* 16:369-376, 1999.

Hambleton and Turnbull, "Anthrax vaccine development: a continuing story," *Bacterial Vaccines* 13:105-122, 1990.

Hemilä et al., "Improving the production of *E. coli* β-lactamase in *Bacillus subtilis*: the effect of glucose, pH and temperature on the production level," *J. Biotechnol.* 26:245-256, 1992.

Iacono-Connors et al., "Expression of the *Bacillus anthracis* protective antigen gene by baculovirus vaccinia virus recombinants," *Infect. Immun.* 58:366-372, 1990.

Ivins et al., "Comparative efficacy of experimental anthrax vaccine candidates against inhalation anthrax in rhesus macaques," *Vaccine* 16:1141-1148, 1998.

Ivins and Welkos, "Cloning and expression of the *Bacillus anthracis* protective antigen gene in *Bacillus subtilis*," *Infect. Immun.* 54:537-542, 1986.

Keppie et al., "The chemical basis of the virulence of *Bacillus anthracis*,IX. Its aggressins and their mode of action," *Br. J. Exp. Pathol.* 44:446-453, 1963.

Kossaczka et al., "Synthesis and immunological properties of Vi and Di-*O*-Acetyl pectin protein conjugates with adipic acid dihydrazide as the linker," *Infect. Immun.* 65:2088-2093, 1997.

Leppla, "Production and purification of anthrax toxin," *Methods Enzymol.* 165:103-116, 1988.

Leppla, "The anthrax toxin complex," In: Sourcebook of bacterial protein toxins (Alouf and Freer, eds.), pp. 277-302, Academic Press, Inc., San Diego, CA, 1991.

Leppla, "Anthrax toxins," In: Bacterial toxins and virulence factors in disease, Handbook of natural toxins (Moss et al., eds.), pp. 543-572, Dekker, New York.

Leppla, "A dominant-negative therapy for anthrax," *Nature Med.* 7:659-660, 2001.

Little et al., "Passive protection by polyclonal antibodies against *Bacillus anthracis* infection in guinea pigs," *Infect. Immun.* 65:5171-5175, 1997.

Liu et al., "Targeting of tumor cells by cell surface urokinase plasminogen activator-dependent anthrax toxin," *J. Biol. Chem* 276:17976-17984, 2001.

Liu et al., "Tumor cell-selective cytotoxicity of matrix metalloproteinase-activated anthrax toxin," *Cancer Res.* 60:6061-6067, 2000.

Mancini et al., "Immunological quantitation of antigens by single radial immunodiffusion," *Immunochemistry* 2:235-254, 1965.

Miller et al., "Production and purification of recombinant protective antigen and protective efficacy against *Bacillus anthracis*," *Lett. Appl. Microbiol.* 26:56-60, 1998.

Mock and Fouet, "Anthrax," *Annu. Rev. Microbiol.* 55:647-671, 2001.

Park and Leppla, "Optimized production and purification of *Bacillus anthracis* lethal factor," *Protein Express. and Purif.* 18:293-302, 2000.

Price et al., Protection against anthrax lethal toxin challenge by genetic immunization with a plasmid encoding the lethal factor protein, *Infect. Immun.* 69:4509-4515, 2001.

Puziss et al., "Large-scale production of protective antigen of *Bacillus anthracis* anaerobic cultures," *Appl. Microbiol.* 11:330-334, 1963.

Ramirez et al., Abstract of SIM Meeting, Nov. 1, 2001.

Ramirez et al., "Production, recovery and immunogenicity of the protective antigen from a recombinant strain of *Bacillus anthracis*," *J. Indus. Microbiol. Biotechnol.* 28:232-238, 2002.

Reuveny et al., "Search for correlates of protective immunity conferred by anthrax vaccine," *Infect. Immun.* 69:2888-2893, 2001.

Sharma et al., "Expression and purification of anthrax toxin protective antigen from *Escherichia coli*," *Protein Expr. Purif.* 7:33-38, 1996.

Simonen and Palva, "Protein secretion in *Bacillus* species," *Microbiol. Rev.* 57:109-137, 1993.

Singh et al., "A deleted variant of *Bacillus anthracis* protective antigen is non-toxic and blocks anthrax toxin action in vivo," *J. Biol. Chem.* 264:19103-19107, 1989.

Singh et al., "Study of immunization against anthrax with the purified recombinant protective antigen of *Bacillus anthracis*," *Infect. Immun.* 66:3447-3448, 1998.

Singh et al., "The chymotrypsin-sensitive site, $FFD^{315}$, in anthrax toxin protective antigen is required for translocation of lethal factor," *J. Biol. Chem.* 269:29039-29046, 1994.

Thorne, "Genetics of *Bacillus anthracis*," In: Microbiology (Leive et al.eds), pp. 56-62, American Society for Microbiology, Washington, D.C., 1985.

Turnbull, "Anthrax vaccines: past, present, and future," *Vaccine* 9:533-539, 1991.

Varughese et al., "Identification of a receptor-binding region within domain 4 of the protective antigen component of anthrax toxin," *Inf. Immun.* 67:1860-1865 (1999).

Vodkin and Leppla, "Cloning of the protective antigen gene of *Bacillus anthracis*," *Cell* 34:693-697, 1983.

Welkos et al., "Sequence and analysis of the DNA encoding protective antigen of *Bacillus anthracis*," *Gene* 69:287-300, 1988.

Welkos et al., "The role of antibodies to *Bacillus anthracis* and anthrax toxin components in inhibiting the early stages of infection by anthrax spores," *Microbiol.* 147:1677-1685, 2001.

Worsham and Sowers, "Isolation of an asporogenic (*spoOA*) protective antigen-producing strain of *Bacillus anthracis*," *Can. J. Microbiol.* 45:1-8, 1999.

Zhang et al., "Role of furin in delivery of a CTL epitope of an anthrax toxin-fusion protein," *Microbiol. Immunol.* 45:119-125, 2001.

\* cited by examiner

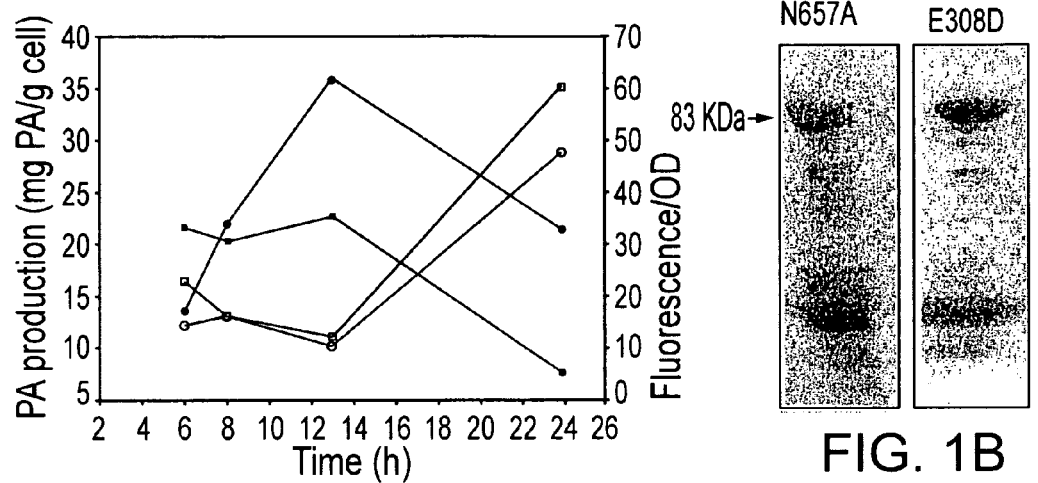
FIG. 1A
FIG. 1B
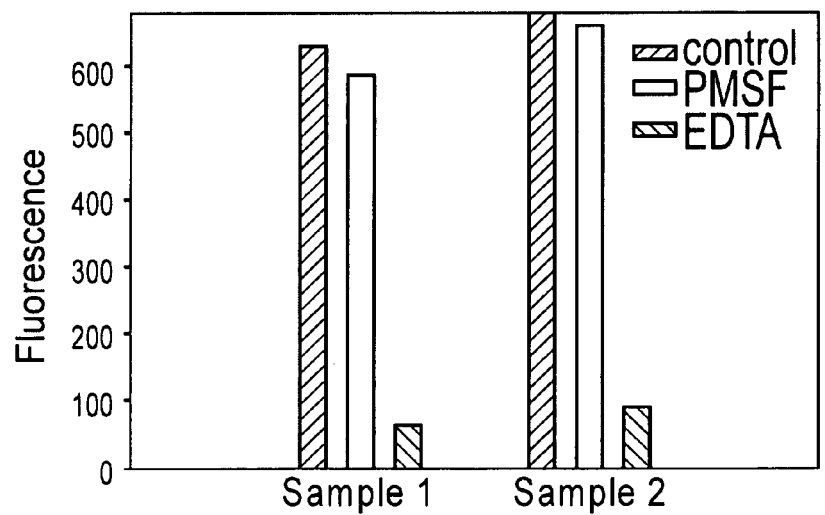
FIG. 2

SEQUENCE LISTING

<160> NUMBER OF SEQ ID NOS: 15

<210> SEQ ID NO 1
<211> LENGTH: 4235
<212> TYPE: DNA
<213> ORGANISM: Bacillus anthracis

```
<220> FEATURE:
<221> NAME/KEY: CDS
<222> LOCATION: (1804)..(4098)

<400> SEQUENCE: 1
aagcttctgt cattcgtaaa tttcaaatag aacgtaaatt tagacttctc atcattaaaa      60
atgaaaaatc ttatcttttt gattctattg tatatttta ttaaggtgtt taatagttag     120
aaaagacagt tgatgctatt actccagata aatatagct aaccataaat ttattaaaga     180
aaccttgttg ttctaaataa tgattttgtg gattccggaa tagatactgg tgagttagct     240
ctaattttat agtgatttaa ctaacaattt ataaagcagc ataattcaaa ttttttaatt     300 gattttcct gaagcatagt ataaaagagt caaggtcttc tagacttgac tcttggaatc     360
attaggaatt aacaatatat ataatgcgct agacagaatc aaattaaatg caaaaatgaa     420
tattttagta agagatccat atcattatga taataacggt aatattgtag gggttgatga     480
ttcatattta aaaaacgcat ataagcaaat acttaattgg tcaagcgatg gagtttcttt     540
aaatctagat gaagatgtaa atcaagcact atctggatat atgcttcaaa taaaaaaacc     600
ttcaaaccac ctaacaaaca gcccagttac aattacatta gcaggcaagg acagtggtgt     660
tggagaattg tatagagtat tatcagatgg agcaggattc ctggatttca ataagtttga     720
tgaaaattgg cgatcattag tagatcctgg tgatgatgtt tatgtgtatg ctgttactaa     780
agaagatttt aatgcagtta ctcgagatga aaatggtaat atagcgaata aattaaaaaa     840
caccttagtt ttatcgggta aaataaaaga aataaacata aaaactacaa atattaatat     900
atttgtagtt tttatgttta ttatataccct cctattttat attattagta gcacagtttt     960
tgcaaatcat gtaattgtat acttatctat gtagaggtat cacaacttat gaatagtgta    1020
ttttattgaa cgttggttag cttggacagt tgtatggata tgcatacttt ataacgtata    1080
aaatttcacg caccacaata aaactaattt aacaaaaaca aaaacacacc taagatcatt    1140
cagttctttt aataaggagc tgcccaccaa gctaaaccta ataatctttt gtttcacata    1200 aggtttttt ctaaatatac agtgtaagtt attgtgaatt taaccagtat atattaaaaa    1260
tgttttatgt taacaaatta aattgtaaaa cccctcttaa gcatagttaa gaggggtagg    1320
ttttaaattt tttgttgaaa ttagaaaaaa taataaaaaa acaaacctat ttctcttcag    1380 gttgttttg ggttacaaaa caaaagaaa acatgtttca aggtacaata attatggttc    1440
tttagctttc tgtaaaacag ccttaatagt tggatttatg actattaaag ttagtataca    1500
gcatacacaa tctattgaag gatatttata atgcaattcc ctaaaaatag ttttgtataa    1560
ccagttcttt tatccgaact gatacacgta ttttagcata attttaatg tatcttcaaa    1620 aacagcttct gtgtcctttt ctattaaaca tataaattct ttttatgtt atatatttat    1680 aaagtctg tttaaaaagc caaaaataaa taattatctc ttttttattta tattatattg    1740 aaactaaagt ttattaattt caatataata taaatttaat tttatacaaa aaggagaacg    1800 tat atg aaa aaa cga aaa gtg tta ata cca tta atg gca ttg tct acg    1848
    Met Lys Lys Arg Lys Val Leu Ile Pro Leu Met Ala Leu Ser Thr
     1               5                  10                  15 ata tta gtt tca agc aca ggt aat tta gag gtg att cag gca gaa gtt    1896
Ile Leu Val Ser Ser Thr Gly Asn Leu Glu Val Ile Gln Ala Glu Val
                20                  25                  30 aaa cag gag aac cgg tta tta aat gaa tca gaa tca agt tcc cag ggg    1944
Lys Gln Glu Asn Arg Leu Leu Asn Glu Ser Glu Ser Ser Gln Gly
             35                  40                  45 tta cta gga tac tat ttt agt gat ttg aat ttt caa gca ccc atg gtg    1992
Leu Leu Gly Tyr Tyr Phe Ser Asp Leu Asn Phe Gln Ala Pro Met Val
```

```
                                          -continued

Leu Leu Gly Tyr Tyr Phe Ser Asp Leu Asn Phe Gln Ala Pro Met Val
         50                  55                  60 gtt acc tct tct act aca ggg gat tta tct att cct agt tct gag tta      2040
Val Thr Ser Ser Thr Thr Gly Asp Leu Ser Ile Pro Ser Ser Glu Leu
 65                  70                  75 gaa aat att cca tcg gaa aac caa tat ttt caa tct gct att tgg tca      2088
Glu Asn Ile Pro Ser Glu Asn Gln Tyr Phe Gln Ser Ala Ile Trp Ser
 80                  85                  90                  95 gga ttt atc aaa gtt aag aag agt gat gaa tat aca ttt gct act tcc      2136
Gly Phe Ile Lys Val Lys Lys Ser Asp Glu Tyr Thr Phe Ala Thr Ser
                100                 105                 110 gct gat aat cat gta aca atg tgg gta gat gac caa gaa gtg att aat      2184
Ala Asp Asn His Val Thr Met Trp Val Asp Asp Gln Glu Val Ile Asn
            115                 120                 125 aaa gct tct aat tct aac aaa atc aga tta gaa aaa gga aga tta tat      2232
Lys Ala Ser Asn Ser Asn Lys Ile Arg Leu Glu Lys Gly Arg Leu Tyr
        130                 135                 140 caa ata aaa att caa tat caa cga gaa aat cct act gaa aaa gga ttg      2280
Gln Ile Lys Ile Gln Tyr Gln Arg Glu Asn Pro Thr Glu Lys Gly Leu
    145                 150                 155 gat ttc aag ttg tac tgg acc gat tct caa aat aaa aaa gaa gtg att      2328
Asp Phe Lys Leu Tyr Trp Thr Asp Ser Gln Asn Lys Lys Glu Val Ile
160                 165                 170                 175 tct agt gat aac tta caa ttg cca gaa tta aaa caa aaa tct tcg aac      2376
Ser Ser Asp Asn Leu Gln Leu Pro Glu Leu Lys Gln Lys Ser Ser Asn
                180                 185                 190 tca aga aaa aag cga agt aca agt gct gga cct acg gtt cca gac cgt      2424
Ser Arg Lys Lys Arg Ser Thr Ser Ala Gly Pro Thr Val Pro Asp Arg
            195                 200                 205 gac aat gat gga atc cct gat tca tta gag gta gaa gga tat acg gtt      2472
Asp Asn Asp Gly Ile Pro Asp Ser Leu Glu Val Glu Gly Tyr Thr Val
        210                 215                 220 gat gtc aaa aat aaa aga act ttt ctt tca cca tgg att tct aat att      2520
Asp Val Lys Asn Lys Arg Thr Phe Leu Ser Pro Trp Ile Ser Asn Ile
    225                 230                 235 cat gaa aag aaa gga tta acc aaa tat aaa tca tct cct gaa aaa tgg      2568
His Glu Lys Lys Gly Leu Thr Lys Tyr Lys Ser Ser Pro Glu Lys Trp
240                 245                 250                 255 agc acg gct tct gat ccg tac agt gat ttc gaa aag gtt aca gga cgg      2616
Ser Thr Ala Ser Asp Pro Tyr Ser Asp Phe Glu Lys Val Thr Gly Arg
                260                 265                 270 att gat aag aat gta tca cca gag gca aga cac ccc ctt gtg gca gct      2664
Ile Asp Lys Asn Val Ser Pro Glu Ala Arg His Pro Leu Val Ala Ala
            275                 280                 285 tat ccg att gta cat gta gat atg gag aat att att ctc tca aaa aat      2712
Tyr Pro Ile Val His Val Asp Met Glu Asn Ile Ile Leu Ser Lys Asn
        290                 295                 300 gag gat caa tcc aca cag aat act gat agt gaa acg aga aca ata agt      2760
Glu Asp Gln Ser Thr Gln Asn Thr Asp Ser Glu Thr Arg Thr Ile Ser
    305                 310                 315 aaa aat act tct aca agt agg aca cat act agt gaa gta cat gga aat      2808
Lys Asn Thr Ser Thr Ser Arg Thr His Thr Ser Glu Val His Gly Asn
320                 325                 330                 335 gca gaa gtg cat gcg tcg ttc ttt gat att ggt ggg agt gta tct gca      2856
Ala Glu Val His Ala Ser Phe Phe Asp Ile Gly Gly Ser Val Ser Ala
                340                 345                 350 gga ttt agt aat tcg aat tca agt acg gtc gca att gat cat tca cta      2904
Gly Phe Ser Asn Ser Asn Ser Ser Thr Val Ala Ile Asp His Ser Leu
            355                 360                 365
```

-continued

```
tct cta gca ggg gaa aga act tgg gct gaa aca atg ggt tta aat acc      2952
Ser Leu Ala Gly Glu Arg Thr Trp Ala Glu Thr Met Gly Leu Asn Thr
        370                 375                 380 gct gat aca gca aga tta aat gcc aat att aga tat gta aat act ggg      3000
Ala Asp Thr Ala Arg Leu Asn Ala Asn Ile Arg Tyr Val Asn Thr Gly
385                 390                 395 acg gct cca atc tac aac gtg tta cca acg act tcg tta gtg tta gga      3048
Thr Ala Pro Ile Tyr Asn Val Leu Pro Thr Thr Ser Leu Val Leu Gly
400                 405                 410                 415 aaa aat caa aca ctc gcg aca att aaa gct aag gaa aac caa tta agt      3096
Lys Asn Gln Thr Leu Ala Thr Ile Lys Ala Lys Glu Asn Gln Leu Ser
                420                 425                 430 caa ata ctt gca cct aat aat tat tat cct tct aaa aac ttg gcg cca      3144
Gln Ile Leu Ala Pro Asn Asn Tyr Tyr Pro Ser Lys Asn Leu Ala Pro
        435                 440                 445 atc gca tta aat gca caa gac gat ttc agt tct act cca att aca atg      3192
Ile Ala Leu Asn Ala Gln Asp Asp Phe Ser Ser Thr Pro Ile Thr Met
450                 455                 460 aat tac aat caa ttt ctt gag tta gaa aaa acg aaa caa tta aga tta      3240
Asn Tyr Asn Gln Phe Leu Glu Leu Glu Lys Thr Lys Gln Leu Arg Leu
465                 470                 475 gat acg gat caa gta tat ggg aat ata gca aca tac aat ttt gaa aat      3288
Asp Thr Asp Gln Val Tyr Gly Asn Ile Ala Thr Tyr Asn Phe Glu Asn
480                 485                 490                 495 gga aga gtg agg gtg gat aca ggc tcg aac tgg agt gaa gtg tta ccg      3336
Gly Arg Val Arg Val Asp Thr Gly Ser Asn Trp Ser Glu Val Leu Pro
                500                 505                 510 caa att caa gaa aca act gca cgt atc att ttt aat gga aaa gat tta      3384
Gln Ile Gln Glu Thr Thr Ala Arg Ile Ile Phe Asn Gly Lys Asp Leu
        515                 520                 525 aat ctg gta gaa agg cgg ata gcg gcg gtt aat cct agt gat cca tta      3432
Asn Leu Val Glu Arg Arg Ile Ala Ala Val Asn Pro Ser Asp Pro Leu
530                 535                 540 gaa acg act aaa ccg gat atg aca tta aaa gaa gcc ctt aaa ata gca      3480
Glu Thr Thr Lys Pro Asp Met Thr Leu Lys Glu Ala Leu Lys Ile Ala
545                 550                 555 ttt gga ttt aac gaa ccg aat gga aac tta caa tat caa ggg aaa gac      3528
Phe Gly Phe Asn Glu Pro Asn Gly Asn Leu Gln Tyr Gln Gly Lys Asp
560                 565                 570                 575 ata acc gaa ttt gat ttt aat ttc gat caa caa aca tct caa aat atc      3576
Ile Thr Glu Phe Asp Phe Asn Phe Asp Gln Gln Thr Ser Gln Asn Ile
                580                 585                 590 aag aat cag tta gcg gaa tta aac gca act aac ata tat act gta tta      3624
Lys Asn Gln Leu Ala Glu Leu Asn Ala Thr Asn Ile Tyr Thr Val Leu
        595                 600                 605 gat aaa atc aaa tta aat gca aaa atg aat att tta ata aga gat aaa      3672
Asp Lys Ile Lys Leu Asn Ala Lys Met Asn Ile Leu Ile Arg Asp Lys
610                 615                 620 cgt ttt cat tat gat aga aat aac ata gca gtt ggg gcg gat gag tca      3720
Arg Phe His Tyr Asp Arg Asn Asn Ile Ala Val Gly Ala Asp Glu Ser
625                 630                 635 gta gtt aag gag gct cat aga gaa gta att aat tcg tca aca gag gga      3768
Val Val Lys Glu Ala His Arg Glu Val Ile Asn Ser Ser Thr Glu Gly
640                 645                 650                 655 tta ttg tta aat att gat aag gat ata aga aaa ata tta tca ggt tat      3816
Leu Leu Leu Asn Ile Asp Lys Asp Ile Arg Lys Ile Leu Ser Gly Tyr
                660                 665                 670 att gta gaa att gaa gat act gaa ggg ctt aaa gaa gtt ata aat gac      3864
Ile Val Glu Ile Glu Asp Thr Glu Gly Leu Lys Glu Val Ile Asn Asp
        675                 680                 685
```

-continued

```
aga tat gat atg ttg aat att tct agt tta cgg caa gat gga aaa aca        3912
Arg Tyr Asp Met Leu Asn Ile Ser Ser Leu Arg Gln Asp Gly Lys Thr
        690                 695                 700 ttt ata gat ttt aaa aaa tat aat gat aaa tta ccg tta tat ata agt        3960
Phe Ile Asp Phe Lys Lys Tyr Asn Asp Lys Leu Pro Leu Tyr Ile Ser
705                 710                 715 aat ccc aat tat aag gta aat gta tat gct gtt act aaa gaa aac act        4008
Asn Pro Asn Tyr Lys Val Asn Val Tyr Ala Val Thr Lys Glu Asn Thr
720                 725                 730                 735 att att aat cct agt gag aat ggg gat act agt acc aac ggg atc aag        4056
Ile Ile Asn Pro Ser Glu Asn Gly Asp Thr Ser Thr Asn Gly Ile Lys
            740                 745                 750 aaa att tta atc ttt tct aaa aaa ggc tat gag ata gga taa               4098
Lys Ile Leu Ile Phe Ser Lys Lys Gly Tyr Glu Ile Gly
            755                 760 ggtaattcta ggtgattttt aaattatcta aaaaacagta aaattaaaac atactctttt     4158
tgtaagaaat acaaggagag tatgttttaa acagtaatct aaatcatcat aatcctttga     4218
gattgtttgt aggatcc                                                    4235

<210> SEQ ID NO 2
<211> LENGTH: 764
<212> TYPE: PRT
<213> ORGANISM: Bacillus anthracis

<400> SEQUENCE: 2

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
    210                 215                 220

Val Lys Asn Lys Arg Thr Phe Leu Ser Pro Trp Ile Ser Asn Ile His
225                 230                 235                 240
```

-continued

```
Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
    290                 295                 300

Asp Gln Ser Thr Gln Asn Thr Asp Ser Glu Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
        355                 360                 365

Leu Ala Gly Glu Arg Thr Trp Ala Glu Thr Met Gly Leu Asn Thr Ala
    370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
        435                 440                 445

Ala Leu Asn Ala Gln Asp Asp Phe Ser Ser Thr Pro Ile Thr Met Asn
    450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
    530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655
```

```
Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
            675                 680                 685

Tyr Asp Met Leu Asn Ile Ser Ser Leu Arg Gln Asp Gly Lys Thr Phe
690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
            725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
            755                 760

<210> SEQ ID NO 3
<211> LENGTH: 735
<212> TYPE: PRT
<213> ORGANISM: Bacillus anthracis

<400> SEQUENCE: 3

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
            35                  40                  45

Glu Leu Glu Asn Ile Pro Ser Glu Asn Gln Tyr Phe Gln Ser Ala Ile
        50                  55                  60

Trp Ser Gly Phe Ile Lys Val Lys Lys Ser Asp Glu Tyr Thr Phe Ala
65              70                  75                  80

Thr Ser Ala Asp Asn His Val Thr Met Trp Val Asp Asp Gln Glu Val
            85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
            115                 120                 125

Gly Leu Asp Phe Lys Leu Tyr Trp Thr Asp Ser Gln Asn Lys Lys Glu
            130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
            165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
            195                 200                 205

Asn Ile His Glu Lys Lys Gly Leu Thr Lys Tyr Lys Ser Ser Pro Glu
            210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
            245                 250                 255

Ala Ala Tyr Pro Ile Val His Val Asp Met Glu Asn Ile Ile Leu Ser
            260                 265                 270
```

```
Lys Asn Glu Asp Gln Ser Thr Gln Asn Thr Asp Ser Glu Thr Arg Thr
            275                 280                 285

Ile Ser Lys Asn Thr Ser Thr Ser Arg Thr His Thr Ser Glu Val His
        290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
        370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
        530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
        610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685
```

```
Ile Ser Asn Pro Asn Tyr Lys Val Asn Val Tyr Ala Val Thr Lys Glu
    690             695                 700

Asn Thr Ile Ile Asn Pro Ser Glu Asn Gly Asp Thr Ser Thr Asn Gly
705             710                 715                 720

Ile Lys Lys Ile Leu Ile Phe Ser Lys Lys Gly Tyr Glu Ile Gly
            725             730                 735

<210> SEQ ID NO 4
<211> LENGTH: 733
<212> TYPE: PRT
<213> ORGANISM: Artificial
<220> FEATURE:
<223> OTHER INFORMATION: PA-SNKE-deltaFF-E308D

<400> SEQUENCE: 4

Glu Val Lys Gln Glu Asn Arg Leu Leu Asn Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val

-continued

```
Gly Phe Ser Asn Ser Asn Ser Ser Thr Val Ala Ile Asp His Ser Leu
            325                 330                 335

Ser Leu Ala Gly Glu Arg Thr Trp Ala Glu Thr Met Gly Leu Asn Thr
        340                 345                 350

Ala Asp Thr Ala Arg Leu Asn Ala Asn Ile Arg Tyr Val Asn Thr Gly
                355                 360                 365

Thr Ala Pro Ile Tyr Asn Val Leu Pro Thr Thr Ser Leu Val Leu Gly
    370                 375                 380

Lys Asn Gln Thr Leu Ala Thr Ile Lys Ala Lys Glu Asn Gln Leu Ser
385                 390                 395                 400

Gln Ile Leu Ala Pro Asn Asn Tyr Tyr Pro Ser Lys Asn Leu Ala Pro
                405                 410                 415

Ile Ala Leu Asn Ala Gln Asp Asp Phe Ser Ser Thr Pro Ile Thr Met
                420                 425                 430

Asn Tyr Asn Gln Phe Leu Glu Leu Glu Lys Thr Lys Gln Leu Arg Leu
            435                 440                 445

Asp Thr Asp Gln Val Tyr Gly Asn Ile Ala Thr Tyr Asn Phe Glu Asn
    450                 455                 460

Gly Arg Val Arg Val Asp Thr Gly Ser Asn Trp Ser Glu Val Leu Pro
465                 470                 475                 480

Gln Ile Gln Glu Thr Thr Ala Arg Ile Ile Phe Asn Gly Lys Asp Leu
                485                 490                 495

Asn Leu Val Glu Arg Arg Ile Ala Ala Val Asn Pro Ser Asp Pro Leu
            500                 505                 510

Glu Thr Thr Lys Pro Asp Met Thr Leu Lys Glu Ala Leu Lys Ile Ala
    515                 520                 525

Phe Gly Phe Asn Glu Pro Asn Gly Asn Leu Gln Tyr Gln Gly Lys Asp
530                 535                 540

Ile Thr Glu Phe Asp Phe Asn Phe Asp Gln Gln Thr Ser Gln Asn Ile
545                 550                 555                 560

Lys Asn Gln Leu Ala Glu Leu Asn Ala Thr Asn Ile Tyr Thr Val Leu
                565                 570                 575

Asp Lys Ile Lys Leu Asn Ala Lys Met Asn Ile Leu Ile Arg Asp Lys
            580                 585                 590

Arg Phe His Tyr Asp Arg Asn Asn Ile Ala Val Gly Ala Asp Glu Ser
        595                 600                 605

Val Val Lys Glu Ala His Arg Glu Val Ile Asn Ser Ser Thr Glu Gly
    610                 615                 620

Leu Leu Leu Asn Ile Asp Lys Asp Ile Arg Lys Ile Leu Ser Gly Tyr
625                 630                 635                 640

Ile Val Glu Ile Glu Asp Thr Glu Gly Leu Lys Glu Val Ile Asn Asp
                645                 650                 655

Arg Tyr Asp Met Leu Asn Ile Ser Ser Leu Arg Gln Asp Gly Lys Thr
            660                 665                 670

Phe Ile Asp Phe Lys Lys Tyr Asn Asp Lys Leu Pro Leu Tyr Ile Ser
        675                 680                 685

Asn Pro Asn Tyr Lys Val Asn Val Tyr Ala Val Thr Lys Glu Asn Thr
    690                 695                 700

Ile Ile Asn Pro Ser Glu Asn Gly Asp Thr Ser Thr Asn Gly Ile Lys
705                 710                 715                 720

Lys Ile Leu Ile Phe Ser Lys Lys Gly Tyr Glu Ile Gly
                725                 730
```

<210> SEQ ID NO 5
<211> LENGTH: 735
<212> TYPE: PRT
<213> ORGANISM: Artificial
<220> FEATURE:
<223> OTHER INFORMATION: PA-N657A

<400> SEQUENCE: 5

| | | | | | | | | | | | | | | |
|---|---|---|---|---|---|---|---|---|---|---|---|---|---|---|
| Glu | Val | Lys | Gln | Glu | Asn | Arg | Leu | Leu | Asn | Glu | Ser | Glu | Ser | Ser |
| 1 | | | | 5 | | | | | 10 | | | | | 15 |
| Gln | Gly | Leu | Leu | Gly | Tyr | Tyr | Phe | Ser | Asp | Leu | Asn | Phe | Gln | Ala | Pro |
| | | | 20 | | | | | 25 | | | | | 30 | | |
| Met | Val | Thr | Ser | Ser | Thr | Thr | Gly | Asp | Leu | Ser | Ile | Pro | Ser | Ser |
| | | | 35 | | | | 40 | | | | | 45 | | |
| Glu | Leu | Glu | Asn | Ile | Pro | Ser | Glu | Asn | Gln | Tyr | Phe | Gln | Ser | Ala | Ile |
| | 50 | | | | | 55 | | | | | 60 | | | | |
| Trp | Ser | Gly | Phe | Ile | Lys | Val | Lys | Lys | Ser | Asp | Glu | Tyr | Thr | Phe | Ala |
| 65 | | | | | 70 | | | | | 75 | | | | | 80 |
| Thr | Ser | Ala | Asp | Asn | His | Val | Thr | Met | Trp | Val | Asp | Asp | Gln | Glu | Val |
| | | | | 85 | | | | | 90 | | | | | 95 | |
| Ile | Asn | Lys | Ala | Ser | Asn | Ser | Asn | Lys | Ile | Arg | Leu | Glu | Lys | Gly | Arg |
| | | | 100 | | | | | 105 | | | | | 110 | | |
| Leu | Tyr | Gln | Ile | Lys | Ile | Gln | Tyr | Gln | Arg | Glu | Asn | Pro | Thr | Glu | Lys |
| | | | 115 | | | | | 120 | | | | | 125 | | |
| Gly | Leu | Asp | Phe | Lys | Leu | Tyr | Trp | Thr | Asp | Ser | Gln | Asn | Lys | Lys | Glu |
| | 130 | | | | | 135 | | | | | 140 | | | | |
| Val | Ile | Ser | Ser | Asp | Asn | Leu | Gln | Leu | Pro | Glu | Leu | Lys | Gln | Lys | Ser |
| 145 | | | | | 150 | | | | | 155 | | | | | 160 |
| Ser | Asn | Ser | Arg | Lys | Lys | Arg | Ser | Thr | Ser | Ala | Gly | Pro | Thr | Val | Pro |
| | | | | 165 | | | | | 170 | | | | | 175 | |
| Asp | Arg | Asp | Asn | Asp | Gly | Ile | Pro | Asp | Ser | Leu | Glu | Val | Glu | Gly | Tyr |
| | | | 180 | | | | | 185 | | | | | 190 | | |
| Thr | Val | Asp | Val | Lys | Asn | Lys | Arg | Thr | Phe | Leu | Ser | Pro | Trp | Ile | Ser |
| | | | 195 | | | | | 200 | | | | | 205 | | |
| Asn | Ile | His | Glu | Lys | Lys | Gly | Leu | Thr | Lys | Tyr | Lys | Ser | Ser | Pro | Glu |
| | 210 | | | | | 215 | | | | | 220 | | | | |
| Lys | Trp | Ser | Thr | Ala | Ser | Asp | Pro | Tyr | Ser | Asp | Phe | Glu | Lys | Val | Thr |
| 225 | | | | | 230 | | | | | 235 | | | | | 240 |
| Gly | Arg | Ile | Asp | Lys | Asn | Val | Ser | Pro | Glu | Ala | Arg | His | Pro | Leu | Val |
| | | | | 245 | | | | | 250 | | | | | 255 | |
| Ala | Ala | Tyr | Pro | Ile | Val | His | Val | Asp | Met | Glu | Asn | Ile | Ile | Leu | Ser |
| | | | 260 | | | | | 265 | | | | | 270 | | |
| Lys | Asn | Glu | Asp | Gln | Ser | Thr | Gln | Asn | Thr | Asp | Ser | Glu | Thr | Arg | Thr |
| | | | 275 | | | | | 280 | | | | | 285 | | |
| Ile | Ser | Lys | Asn | Thr | Ser | Thr | Ser | Arg | Thr | His | Thr | Ser | Glu | Val | His |
| | 290 | | | | | 295 | | | | | 300 | | | | |
| Gly | Asn | Ala | Glu | Val | His | Ala | Ser | Phe | Phe | Asp | Ile | Gly | Gly | Ser | Val |
| 305 | | | | | 310 | | | | | 315 | | | | | 320 |
| Ser | Ala | Gly | Phe | Ser | Asn | Ser | Asn | Ser | Ser | Thr | Val | Ala | Ile | Asp | His |
| | | | | 325 | | | | | 330 | | | | | 335 | |
| Ser | Leu | Ser | Leu | Ala | Gly | Glu | Arg | Thr | Trp | Ala | Glu | Thr | Met | Gly | Leu |
| | | | 340 | | | | | 345 | | | | | 350 | | |
| Asn | Thr | Ala | Asp | Thr | Ala | Arg | Leu | Asn | Ala | Asn | Ile | Arg | Tyr | Val | Asn |
| | | | 355 | | | | | 360 | | | | | 365 | | |
| Thr | Gly | Thr | Ala | Pro | Ile | Tyr | Asn | Val | Leu | Pro | Thr | Thr | Ser | Leu | Val |

```
            370                 375                 380
Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Ala Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735
```

<210> SEQ ID NO 6
<211> LENGTH: 735
<212> TYPE: PRT
<213> ORGANISM: Artificial
<220> FEATURE:
<223> OTHER INFORMATION: K397D D425K mutant

<400> SEQUENCE: 6

Glu Val Lys Gln Glu Asn Arg Leu Leu Asn Glu Ser Glu Ser Ser Ser

-continued

```
1               5               10              15
Gln Gly Leu Leu Gly Tyr Tyr Phe Ser Asp Leu Asn Phe Gln Ala Pro
                20              25              30

Met Val Val Thr Ser Ser Thr Thr Gly Asp Leu Ser Ile Pro Ser Ser
                35              40              45

Glu Leu Glu Asn Ile Pro Ser Glu Asn Gln Tyr Phe Gln Ser Ala Ile
        50              55              60

Trp Ser Gly Phe Ile Lys Val Lys Lys Ser Asp Glu Tyr Thr Phe Ala
65              70              75              80

Thr Ser Ala Asp Asn His Val Thr Met Trp Val Asp Asp Gln Glu Val
                85              90              95

Ile Asn Lys Ala Ser Asn Ser Asn Lys Ile Arg Leu Glu Lys Gly Arg
                100             105             110

Leu Tyr Gln Ile Lys Ile Gln Tyr Gln Arg Glu Asn Pro Thr Glu Lys
        115             120             125

Gly Leu Asp Phe Lys Leu Tyr Trp Thr Asp Ser Gln Asn Lys Lys Glu
        130             135             140

Val Ile Ser Ser Asp Asn Leu Gln Leu Pro Glu Leu Lys Gln Lys Ser
145             150             155             160

Ser Asn Ser Arg Lys Lys Arg Ser Thr Ser Ala Gly Pro Thr Val Pro
                165             170             175

Asp Arg Asp Asn Asp Gly Ile Pro Asp Ser Leu Glu Val Glu Gly Tyr
                180             185             190

Thr Val Asp Val Lys Asn Lys Arg Thr Phe Leu Ser Pro Trp Ile Ser
        195             200             205

Asn Ile His Glu Lys Lys Gly Leu Thr Lys Tyr Lys Ser Ser Pro Glu
        210             215             220

Lys Trp Ser Thr Ala Ser Asp Pro Tyr Ser Asp Phe Glu Lys Val Thr
225             230             235             240

Gly Arg Ile Asp Lys Asn Val Ser Pro Glu Ala Arg His Pro Leu Val
                245             250             255

Ala Ala Tyr Pro Ile Val His Val Asp Met Glu Asn Ile Ile Leu Ser
                260             265             270

Lys Asn Glu Asp Gln Ser Thr Gln Asn Thr Asp Ser Glu Thr Arg Thr
        275             280             285

Ile Ser Lys Asn Thr Ser Thr Ser Arg Thr His Thr Ser Glu Val His
        290             295             300

Gly Asn Ala Glu Val His Ala Ser Phe Phe Asp Ile Gly Gly Ser Val
305             310             315             320

Ser Ala Gly Phe Ser Asn Ser Asn Ser Ser Thr Val Ala Ile Asp His
                325             330             335

Ser Leu Ser Leu Ala Gly Glu Arg Thr Trp Ala Glu Thr Met Gly Leu
                340             345             350

Asn Thr Ala Asp Thr Ala Arg Leu Asn Ala Asn Ile Arg Tyr Val Asn
        355             360             365

Thr Gly Thr Ala Pro Ile Tyr Asn Val Leu Pro Thr Thr Ser Leu Val
        370             375             380

Leu Gly Lys Asn Gln Thr Leu Ala Thr Ile Lys Ala Asp Glu Asn Gln
385             390             395             400

Leu Ser Gln Ile Leu Ala Pro Asn Asn Tyr Tyr Pro Ser Lys Asn Leu
                405             410             415

Ala Pro Ile Ala Leu Asn Ala Gln Lys Asp Phe Ser Ser Thr Pro Ile
                420             425             430
```

```
Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735

<210> SEQ ID NO 7
<211> LENGTH: 739
<212> TYPE: PRT
<213> ORGANISM: Artificial
<220> FEATURE:
<223> OTHER INFORMATION: PA-L1 with MMP cleavage site

<400> SEQUENCE: 7

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60
```

-continued

```
Trp Ser Gly Phe Ile Lys Val Lys Ser Asp Glu Tyr Thr Phe Ala
 65                  70                  75                  80

Thr Ser Ala Asp Asn His Val Thr Met Trp Val Asp Gln Glu Val
                 85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
            115                 120                 125

Gly Leu Asp Phe Lys Leu Tyr Trp Thr Asp Ser Gln Asn Lys Lys Glu
130                 135                 140

Val Ile Ser Ser Asp Asn Leu Gln Leu Pro Glu Leu Lys Gln Lys Ser
145                 150                 155                 160

Ser Asn Ser Gly Pro Leu Gly Met Leu Ser Gln Ser Thr Ser Ala Gly
                165                 170                 175

Pro Thr Val Pro Asp Arg Asp Asn Asp Gly Ile Pro Asp Ser Leu Glu
            180                 185                 190

Val Glu Gly Tyr Thr Val Asp Val Lys Asn Lys Arg Thr Phe Leu Ser
            195                 200                 205

Pro Trp Ile Ser Asn Ile His Glu Lys Lys Gly Leu Thr Lys Tyr Lys
210                 215                 220

Ser Ser Pro Glu Lys Trp Ser Thr Ala Ser Asp Pro Tyr Ser Asp Phe
225                 230                 235                 240

Glu Lys Val Thr Gly Arg Ile Asp Lys Asn Val Ser Pro Glu Ala Arg
            245                 250                 255

His Pro Leu Val Ala Ala Tyr Pro Ile Val His Val Asp Met Glu Asn
            260                 265                 270

Ile Ile Leu Ser Lys Asn Glu Asp Gln Ser Thr Gln Asn Thr Asp Ser
            275                 280                 285

Glu Thr Arg Thr Ile Ser Lys Asn Thr Ser Thr Ser Arg Thr His Thr
290                 295                 300

Ser Glu Val His Gly Asn Ala Glu Val His Ala Ser Phe Phe Asp Ile
305                 310                 315                 320

Gly Gly Ser Val Ser Ala Gly Phe Ser Asn Ser Asn Ser Ser Thr Val
            325                 330                 335

Ala Ile Asp His Ser Leu Ser Leu Ala Gly Glu Arg Thr Trp Ala Glu
            340                 345                 350

Thr Met Gly Leu Asn Thr Ala Asp Thr Ala Arg Leu Asn Ala Asn Ile
            355                 360                 365

Arg Tyr Val Asn Thr Gly Thr Ala Pro Ile Tyr Asn Val Leu Pro Thr
370                 375                 380

Thr Ser Leu Val Leu Gly Lys Asn Gln Thr Leu Ala Thr Ile Lys Ala
385                 390                 395                 400

Lys Glu Asn Gln Leu Ser Gln Ile Leu Ala Pro Asn Asn Tyr Tyr Pro
            405                 410                 415

Ser Lys Asn Leu Ala Pro Ile Ala Leu Asn Ala Gln Asp Asp Phe Ser
            420                 425                 430

Ser Thr Pro Ile Thr Met Asn Tyr Asn Gln Phe Leu Glu Leu Glu Lys
            435                 440                 445

Thr Lys Gln Leu Arg Leu Asp Thr Asp Gln Val Tyr Gly Asn Ile Ala
            450                 455                 460

Thr Tyr Asn Phe Glu Asn Gly Arg Val Arg Val Asp Thr Gly Ser Asn
465                 470                 475                 480
```

```
Trp Ser Glu Val Leu Pro Gln Ile Gln Glu Thr Thr Ala Arg Ile Ile
                485                 490                 495

Phe Asn Gly Lys Asp Leu Asn Leu Val Glu Arg Arg Ile Ala Ala Val
            500                 505                 510

Asn Pro Ser Asp Pro Leu Glu Thr Thr Lys Pro Asp Met Thr Leu Lys
        515                 520                 525

Glu Ala Leu Lys Ile Ala Phe Gly Phe Asn Glu Pro Asn Gly Asn Leu
    530                 535                 540

Gln Tyr Gln Gly Lys Asp Ile Thr Glu Phe Asp Phe Asn Phe Asp Gln
545                 550                 555                 560

Gln Thr Ser Gln Asn Ile Lys Asn Gln Leu Ala Glu Leu Asn Ala Thr
                565                 570                 575

Asn Ile Tyr Thr Val Leu Asp Lys Ile Lys Leu Asn Ala Lys Met Asn
            580                 585                 590

Ile Leu Ile Arg Asp Lys Arg Phe His Tyr Asp Arg Asn Asn Ile Ala
        595                 600                 605

Val Gly Ala Asp Glu Ser Val Val Lys Glu Ala His Arg Glu Val Ile
    610                 615                 620

Asn Ser Ser Thr Glu Gly Leu Leu Leu Asn Ile Asp Lys Asp Ile Arg
625                 630                 635                 640

Lys Ile Leu Ser Gly Tyr Ile Val Glu Ile Glu Asp Thr Glu Gly Leu
                645                 650                 655

Lys Glu Val Ile Asn Asp Arg Tyr Asp Met Leu Asn Ile Ser Ser Leu
            660                 665                 670

Arg Gln Asp Gly Lys Thr Phe Ile Asp Phe Lys Lys Tyr Asn Asp Lys
        675                 680                 685

Leu Pro Leu Tyr Ile Ser Asn Pro Asn Tyr Lys Val Asn Val Tyr Ala
    690                 695                 700

Val Thr Lys Glu Asn Thr Ile Ile Asn Pro Ser Glu Asn Gly Asp Thr
705                 710                 715                 720

Ser Thr Asn Gly Ile Lys Lys Ile Leu Ile Phe Ser Lys Lys Gly Tyr
                725                 730                 735

Glu Ile Gly

<210> SEQ ID NO 8
<211> LENGTH: 739
<212> TYPE: PRT
<213> ORGANISM: Artificial
<220> FEATURE:
<223> OTHER INFORMATION: PA-L2 cleavable with MMP

<400> SEQUENCE: 8

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
```

-continued

```
                100                 105                 110
Leu Tyr Gln Ile Lys Ile Gln Tyr Gln Arg Glu Asn Pro Thr Glu Lys
            115                 120                 125
Gly Leu Asp Phe Lys Leu Tyr Trp Thr Asp Ser Gln Asn Lys Lys Glu
            130                 135                 140
Val Ile Ser Ser Asp Asn Leu Gln Leu Pro Glu Leu Lys Gln Lys Ser
145                 150                 155                 160
Ser Asn Ser Gly Pro Leu Gly Leu Trp Ala Gln Ser Thr Ser Ala Gly
                165                 170                 175
Pro Thr Val Pro Asp Arg Asp Asn Asp Gly Ile Pro Asp Ser Leu Glu
            180                 185                 190
Val Glu Gly Tyr Thr Val Asp Val Lys Asn Lys Arg Thr Phe Leu Ser
            195                 200                 205
Pro Trp Ile Ser Asn Ile His Glu Lys Lys Gly Leu Thr Lys Tyr Lys
        210                 215                 220
Ser Ser Pro Glu Lys Trp Ser Thr Ala Ser Asp Pro Tyr Ser Asp Phe
225                 230                 235                 240
Glu Lys Val Thr Gly Arg Ile Asp Lys Asn Val Ser Pro Glu Ala Arg
                245                 250                 255
His Pro Leu Val Ala Ala Tyr Pro Ile Val His Val Asp Met Glu Asn
            260                 265                 270
Ile Ile Leu Ser Lys Asn Glu Asp Gln Ser Thr Gln Asn Thr Asp Ser
        275                 280                 285
Glu Thr Arg Thr Ile Ser Lys Asn Thr Ser Thr Arg Thr His Thr
    290                 295                 300
Ser Glu Val His Gly Asn Ala Glu Val His Ala Ser Phe Phe Asp Ile
305                 310                 315                 320
Gly Gly Ser Val Ser Ala Gly Phe Ser Asn Ser Asn Ser Ser Thr Val
                325                 330                 335
Ala Ile Asp His Ser Leu Ser Leu Ala Gly Glu Arg Thr Trp Ala Glu
            340                 345                 350
Thr Met Gly Leu Asn Thr Ala Asp Thr Ala Arg Leu Asn Ala Asn Ile
        355                 360                 365
Arg Tyr Val Asn Thr Gly Thr Ala Pro Ile Tyr Asn Val Leu Pro Thr
    370                 375                 380
Thr Ser Leu Val Leu Gly Lys Asn Gln Thr Leu Ala Thr Ile Lys Ala
385                 390                 395                 400
Lys Glu Asn Gln Leu Ser Gln Ile Leu Ala Pro Asn Asn Tyr Tyr Pro
                405                 410                 415
Ser Lys Asn Leu Ala Pro Ile Ala Leu Asn Ala Gln Asp Asp Phe Ser
            420                 425                 430
Ser Thr Pro Ile Thr Met Asn Tyr Asn Gln Phe Leu Glu Leu Glu Lys
        435                 440                 445
Thr Lys Gln Leu Arg Leu Asp Thr Asp Gln Val Tyr Gly Asn Ile Ala
    450                 455                 460
Thr Tyr Asn Phe Glu Asn Gly Arg Val Arg Val Asp Thr Gly Ser Asn
465                 470                 475                 480
Trp Ser Glu Val Leu Pro Gln Ile Gln Glu Thr Thr Ala Arg Ile Ile
                485                 490                 495
Phe Asn Gly Lys Asp Leu Asn Leu Val Glu Arg Arg Ile Ala Ala Val
            500                 505                 510
Asn Pro Ser Asp Pro Leu Glu Thr Thr Lys Pro Asp Met Thr Leu Lys
        515                 520                 525
```

-continued

```
Glu Ala Leu Lys Ile Ala Phe Gly Phe Asn Glu Pro Asn Gly Asn Leu
            530                 535                 540
Gln Tyr Gln Gly Lys Asp Ile Thr Glu Phe Asp Phe Asn Phe Asp Gln
545                 550                 555                 560
Gln Thr Ser Gln Asn Ile Lys Asn Gln Leu Ala Glu Leu Asn Ala Thr
                565                 570                 575
Asn Ile Tyr Thr Val Leu Asp Lys Ile Lys Leu Asn Ala Lys Met Asn
            580                 585                 590
Ile Leu Ile Arg Asp Lys Arg Phe His Tyr Asp Arg Asn Asn Ile Ala
            595                 600                 605
Val Gly Ala Asp Glu Ser Val Val Lys Glu Ala His Arg Glu Val Ile
            610                 615                 620
Asn Ser Ser Thr Glu Gly Leu Leu Leu Asn Ile Asp Lys Asp Ile Arg
625                 630                 635                 640
Lys Ile Leu Ser Gly Tyr Ile Val Glu Ile Glu Asp Thr Glu Gly Leu
                645                 650                 655
Lys Glu Val Ile Asn Asp Arg Tyr Asp Met Leu Asn Ile Ser Ser Leu
            660                 665                 670
Arg Gln Asp Gly Lys Thr Phe Ile Asp Phe Lys Lys Tyr Asn Asp Lys
            675                 680                 685
Leu Pro Leu Tyr Ile Ser Asn Pro Asn Tyr Lys Val Asn Val Tyr Ala
            690                 695                 700
Val Thr Lys Glu Asn Thr Ile Ile Asn Pro Ser Glu Asn Gly Asp Thr
705                 710                 715                 720
Ser Thr Asn Gly Ile Lys Lys Ile Leu Ile Phe Ser Lys Lys Gly Tyr
                725                 730                 735
Glu Ile Gly

<210> SEQ ID NO 9
<211> LENGTH: 740
<212> TYPE: PRT
<213> ORGANISM: Artificial
<220> FEATURE:
<223> OTHER INFORMATION: PrAg-U1 cleavable by uPA/tPA

<400> SEQUENCE: 9

Glu Val Lys Gln Glu Asn Arg Leu Leu Asn Glu Ser Glu Ser Ser Ser
1               5                   10                  15
Gln Gly Leu Leu Gly Tyr Tyr Phe Ser Asp Leu Asn Phe Gln Ala Pro
            20                  25                  30
Met Val Val Thr Ser Ser Thr Thr Gly Asp Leu Ser Ile Pro Ser Ser
            35                  40                  45
Glu Leu Glu Asn Ile Pro Ser Glu Asn Gln Tyr Phe Gln Ser Ala Ile
        50                  55                  60
Trp Ser Gly Phe Ile Lys Val Lys Lys Ser Asp Glu Tyr Thr Phe Ala
65                  70                  75                  80
Thr Ser Ala Asp Asn His Val Thr Met Trp Val Asp Asp Gln Glu Val
                85                  90                  95
Ile Asn Lys Ala Ser Asn Ser Asn Lys Ile Arg Leu Glu Lys Gly Arg
            100                 105                 110
Leu Tyr Gln Ile Lys Ile Gln Tyr Gln Arg Glu Asn Pro Thr Glu Lys
            115                 120                 125
Gly Leu Asp Phe Lys Leu Tyr Trp Thr Asp Ser Gln Asn Lys Lys Glu
        130                 135                 140
```

-continued

```
Val Ile Ser Ser Asp Asn Leu Gln Leu Pro Glu Leu Lys Gln Lys Ser
145                 150                 155                 160

Ser Asn Ser Pro Cys Pro Gly Arg Val Val Gly Gly Ser Thr Ser Ala
                165                 170                 175

Gly Pro Thr Val Pro Asp Arg Asp Asn Asp Gly Ile Pro Asp Ser Leu
            180                 185                 190

Glu Val Glu Gly Tyr Thr Val Asp Val Lys Asn Lys Arg Thr Phe Leu
        195                 200                 205

Ser Pro Trp Ile Ser Asn Ile His Glu Lys Lys Gly Leu Thr Lys Tyr
    210                 215                 220

Lys Ser Ser Pro Glu Lys Trp Ser Thr Ala Ser Asp Pro Tyr Ser Asp
225                 230                 235                 240

Phe Glu Lys Val Thr Gly Arg Ile Asp Lys Asn Val Ser Pro Glu Ala
                245                 250                 255

Arg His Pro Leu Val Ala Ala Tyr Pro Ile Val His Val Asp Met Glu
            260                 265                 270

Asn Ile Ile Leu Ser Lys Asn Glu Asp Gln Ser Thr Gln Asn Thr Asp
        275                 280                 285

Ser Glu Thr Arg Thr Ile Ser Lys Asn Thr Ser Thr Ser Arg Thr His
    290                 295                 300

Thr Ser Glu Val His Gly Asn Ala Glu Val His Ala Ser Phe Phe Asp
305                 310                 315                 320

Ile Gly Gly Ser Val Ser Ala Gly Phe Ser Asn Ser Asn Ser Ser Thr
                325                 330                 335

Val Ala Ile Asp His Ser Leu Ser Leu Ala Gly Glu Arg Thr Trp Ala
            340                 345                 350

Glu Thr Met Gly Leu Asn Thr Ala Asp Thr Ala Arg Leu Asn Ala Asn
        355                 360                 365

Ile Arg Tyr Val Asn Thr Gly Thr Ala Pro Ile Tyr Asn Val Leu Pro
    370                 375                 380

Thr Thr Ser Leu Val Leu Gly Lys Asn Gln Thr Leu Ala Thr Ile Lys
385                 390                 395                 400

Ala Lys Glu Asn Gln Leu Ser Gln Ile Leu Ala Pro Asn Asn Tyr Tyr
                405                 410                 415

Pro Ser Lys Asn Leu Ala Pro Ile Ala Leu Asn Ala Gln Asp Asp Phe
            420                 425                 430

Ser Ser Thr Pro Ile Thr Met Asn Tyr Asn Gln Phe Leu Glu Leu Glu
        435                 440                 445

Lys Thr Lys Gln Leu Arg Leu Asp Thr Asp Gln Val Tyr Gly Asn Ile
    450                 455                 460

Ala Thr Tyr Asn Phe Glu Asn Gly Arg Val Arg Val Asp Thr Gly Ser
465                 470                 475                 480

Asn Trp Ser Glu Val Leu Pro Gln Ile Gln Glu Thr Thr Ala Arg Ile
                485                 490                 495

Ile Phe Asn Gly Lys Asp Leu Asn Leu Val Glu Arg Arg Ile Ala Ala
            500                 505                 510

Val Asn Pro Ser Asp Pro Leu Glu Thr Thr Lys Pro Asp Met Thr Leu
        515                 520                 525

Lys Glu Ala Leu Lys Ile Ala Phe Gly Phe Asn Glu Pro Asn Gly Asn
    530                 535                 540

Leu Gln Tyr Gln Gly Lys Asp Ile Thr Glu Phe Asp Phe Asn Phe Asp
545                 550                 555                 560

Gln Gln Thr Ser Gln Asn Ile Lys Asn Gln Leu Ala Glu Leu Asn Ala
```

```
                    565                 570                 575

Thr Asn Ile Tyr Thr Val Leu Asp Lys Ile Lys Leu Asn Ala Lys Met
                580                 585                 590

Asn Ile Leu Ile Arg Asp Lys Arg Phe His Tyr Asp Arg Asn Asn Ile
            595                 600                 605

Ala Val Gly Ala Asp Glu Ser Val Lys Glu Ala His Arg Glu Val
        610                 615                 620

Ile Asn Ser Ser Thr Glu Gly Leu Leu Leu Asn Ile Asp Lys Asp Ile
625                 630                 635                 640

Arg Lys Ile Leu Ser Gly Tyr Ile Val Glu Ile Glu Asp Thr Glu Gly
                645                 650                 655

Leu Lys Glu Val Ile Asn Asp Arg Tyr Asp Met Leu Asn Ile Ser Ser
            660                 665                 670

Leu Arg Gln Asp Gly Lys Thr Phe Ile Asp Phe Lys Lys Tyr Asn Asp
        675                 680                 685

Lys Leu Pro Leu Tyr Ile Ser Asn Pro Asn Tyr Lys Val Asn Val Tyr
    690                 695                 700

Ala Val Thr Lys Glu Asn Thr Ile Ile Asn Pro Ser Glu Asn Gly Asp
705                 710                 715                 720

Thr Ser Thr Asn Gly Ile Lys Lys Ile Leu Ile Phe Ser Lys Lys Gly
                725                 730                 735

Tyr Glu Ile Gly
740

<210> SEQ ID NO 10
<211> LENGTH: 738
<212> TYPE: PRT
<213> ORGANISM: Artificial
<220> FEATURE:
<223> OTHER INFORMATION: PrAg-U2 cleav -continued

```
                180                 185                 190
Glu Gly Tyr Thr Val Asp Val Lys Asn Lys Arg Thr Phe Leu Ser Pro
            195                 200                 205
Trp Ile Ser Asn Ile His Glu Lys Lys Gly Leu Thr Lys Tyr Lys Ser
            210                 215                 220
Ser Pro Glu Lys Trp Ser Thr Ala Ser Asp Pro Tyr Ser Asp Phe Glu
225                 230                 235                 240
Lys Val Thr Gly Arg Ile Asp Lys Asn Val Ser Pro Glu Ala Arg His
                        245                 250                 255
Pro Leu Val Ala Ala Tyr Pro Ile Val His Val Asp Met Glu Asn Ile
                260                 265                 270
Ile Leu Ser Lys Asn Glu Asp Gln Ser Thr Gln Asn Thr Asp Ser Glu
            275                 280                 285
Thr Arg Thr Ile Ser Lys Asn Thr Ser Thr Ser Arg Thr His Thr Ser
        290                 295                 300
Glu Val His Gly Asn Ala Glu Val His Ala Ser Phe Phe Asp Ile Gly
305                 310                 315                 320
Gly Ser Val Ser Ala Gly Phe Ser Asn Ser Asn Ser Ser Thr Val Ala
                    325                 330                 335
Ile Asp His Ser Leu Ser Leu Ala Gly Glu Arg Thr Trp Ala Glu Thr
                340                 345                 350
Met Gly Leu Asn Thr Ala Asp Thr Ala Arg Leu Asn Ala Asn Ile Arg
            355                 360                 365
Tyr Val Asn Thr Gly Thr Ala Pro Ile Tyr Asn Val Leu Pro Thr Thr
        370                 375                 380
Ser Leu Val Leu Gly Lys Asn Gln Thr Leu Ala Thr Ile Lys Ala Lys
385                 390                 395                 400
Glu Asn Gln Leu Ser Gln Ile Leu Ala Pro Asn Asn Tyr Tyr Pro Ser
                    405                 410                 415
Lys Asn Leu Ala Pro Ile Ala Leu Asn Ala Gln Asp Asp Phe Ser Ser
                420                 425                 430
Thr Pro Ile Thr Met Asn Tyr Asn Gln Phe Leu Glu Leu Glu Lys Thr
            435                 440                 445
Lys Gln Leu Arg Leu Asp Thr Asp Gln Val Tyr Gly Asn Ile Ala Thr
        450                 455                 460
Tyr Asn Phe Glu Asn Gly Arg Val Arg Val Asp Thr Gly Ser Asn Trp
465                 470                 475                 480
Ser Glu Val Leu Pro Gln Ile Gln Glu Thr Thr Ala Arg Ile Ile Phe
                    485                 490                 495
Asn Gly Lys Asp Leu Asn Leu Val Glu Arg Arg Ile Ala Ala Val Asn
                500                 505                 510
Pro Ser Asp Pro Leu Glu Thr Thr Lys Pro Asp Met Thr Leu Lys Glu
            515                 520                 525
Ala Leu Lys Ile Ala Phe Gly Phe Asn Glu Pro Asn Gly Asn Leu Gln
        530                 535                 540
Tyr Gln Gly Lys Asp Ile Thr Glu Phe Asp Phe Asn Phe Asp Gln Gln
545                 550                 555                 560
Thr Ser Gln Asn Ile Lys Asn Gln Leu Ala Glu Leu Asn Ala Thr Asn
                    565                 570                 575
Ile Tyr Thr Val Leu Asp Lys Ile Lys Leu Asn Ala Lys Met Asn Ile
                580                 585                 590
Leu Ile Arg Asp Lys Arg Phe His Tyr Asp Arg Asn Asn Ile Ala Val
            595                 600                 605
```

```
Gly Ala Asp Glu Ser Val Val Lys Glu Ala His Arg Glu Val Ile Asn
        610                 615                 620
Ser Ser Thr Glu Gly Leu Leu Leu Asn Ile Asp Lys Asp Ile Arg Lys
625                 630                 635                 640
Ile Leu Ser Gly Tyr Ile Val Glu Ile Glu Asp Thr Glu Gly Leu Lys
                645                 650                 655
Glu Val Ile Asn Asp Arg Tyr Asp Met Leu Asn Ile Ser Ser Leu Arg
            660                 665                 670
Gln Asp Gly Lys Thr Phe Ile Asp Phe Lys Lys Tyr Asn Asp Lys Leu
        675                 680                 685
Pro Leu Tyr Ile Ser Asn Pro Asn Tyr Lys Val Asn Val Tyr Ala Val
    690                 695                 700
Thr Lys Glu Asn Thr Ile Ile Asn Pro Ser Glu Asn Gly Asp Thr Ser
705                 710                 715                 720
Thr Asn Gly Ile Lys Lys Ile Leu Ile Phe Ser Lys Lys Gly Tyr Glu
                725                 730                 735
Ile Gly

<210> SEQ ID NO 11
<211> LENGTH: 738
<212> TYPE: PRT
<213> ORGANISM: Artificial
<220> FEATURE:
<223> OTHER INFORMATION: PrAg-U3 cleavable by uPA

<400> SEQUENCE: 11

Glu Val Lys Gln Glu Asn Arg Leu Leu Asn Glu Ser Glu Ser Ser Ser
1               5                   10                  15
Gln Gly Leu Leu Gly Tyr Tyr Phe Ser Asp Leu Asn Phe Gln Ala Pro
                20                  25                  30
Met Val Val Thr Ser Ser Thr Thr Gly Asp Leu Ser Ile Pro Ser Ser
            35                  40                  45
Glu Leu Glu Asn Ile Pro Ser Glu Asn Gln Tyr Phe Gln Ser Ala Ile
        50                  55                  60
Trp Ser Gly Phe Ile Lys Val Lys Lys Ser Asp Glu Tyr Thr Phe Ala
65                  70                  75                  80
Thr Ser Ala Asp Asn His Val Thr Met Trp Val Asp Asp Gln Glu Val
                85                  90                  95
Ile Asn Lys Ala Ser Asn Ser Asn Lys Ile Arg Leu Glu Lys Gly Arg
            100                 105                 110
Leu Tyr Gln Ile Lys Ile Gln Tyr Gln Arg Glu Asn Pro Thr Glu Lys
        115                 120                 125
Gly Leu Asp Phe Lys Leu Tyr Trp Thr Asp Ser Gln Asn Lys Lys Glu
    130                 135                 140
Val Ile Ser Ser Asp Asn Leu Gln Leu Pro Glu Leu Lys Gln Lys Ser
145                 150                 155                 160
Ser Asn Ser Pro Gly Ser Gly Lys Ser Ala Ser Thr Ser Ala Gly Pro
                165                 170                 175
Thr Val Pro Asp Arg Asp Asn Asp Gly Ile Pro Asp Ser Leu Glu Val
            180                 185                 190
Glu Gly Tyr Thr Val Asp Val Lys Asn Lys Arg Thr Phe Leu Ser Pro
        195                 200                 205
Trp Ile Ser Asn Ile His Glu Lys Lys Gly Leu Thr Lys Tyr Lys Ser
    210                 215                 220
```

-continued

```
Ser Pro Glu Lys Trp Ser Thr Ala Ser Asp Pro Tyr Ser Asp Phe Glu
225                 230                 235                 240

Lys Val Thr Gly Arg Ile Asp Lys Asn Val Ser Pro Glu Ala Arg His
            245                 250                 255

Pro Leu Val Ala Ala Tyr Pro Ile Val His Val Asp Met Glu Asn Ile
        260                 265                 270

Ile Leu Ser Lys Asn Glu Asp Gln Ser Thr Gln Asn Thr Asp Ser Glu
    275                 280                 285

Thr Arg Thr Ile Ser Lys Asn Thr Ser Thr Ser Arg Thr His Thr Ser
290                 295                 300

Glu Val His Gly Asn Ala Glu Val His Ala Ser Phe Phe Asp Ile Gly
305                 310                 315                 320

Gly Ser Val Ser Ala Gly Phe Ser Asn Ser Asn Ser Ser Thr Val Ala
                325                 330                 335

Ile Asp His Ser Leu Ser Leu Ala Gly Glu Arg Thr Trp Ala Glu Thr
            340                 345                 350

Met Gly Leu Asn Thr Ala Asp Thr Ala Arg Leu Asn Ala Asn Ile Arg
        355                 360                 365

Tyr Val Asn Thr Gly Thr Ala Pro Ile Tyr Asn Val Leu Pro Thr Thr
    370                 375                 380

Ser Leu Val Leu Gly Lys Asn Gln Thr Leu Ala Thr Ile Lys Ala Lys
385                 390                 395                 400

Glu Asn Gln Leu Ser Gln Ile Leu Ala Pro Asn Asn Tyr Tyr Pro Ser
                405                 410                 415

Lys Asn Leu Ala Pro Ile Ala Leu Asn Ala Gln Asp Asp Phe Ser Ser
            420                 425                 430

Thr Pro Ile Thr Met Asn Tyr Asn Gln Phe Leu Glu Leu Glu Lys Thr
        435                 440                 445

Lys Gln Leu Arg Leu Asp Thr Asp Gln Val Tyr Gly Asn Ile Ala Thr
    450                 455                 460

Tyr Asn Phe Glu Asn Gly Arg Val Arg Val Asp Thr Gly Ser Asn Trp
465                 470                 475                 480

Ser Glu Val Leu Pro Gln Ile Gln Glu Thr Thr Ala Arg Ile Ile Phe
                485                 490                 495

Asn Gly Lys Asp Leu Asn Leu Val Glu Arg Arg Ile Ala Ala Val Asn
            500                 505                 510

Pro Ser Asp Pro Leu Glu Thr Thr Lys Pro Asp Met Thr Leu Lys Glu
        515                 520                 525

Ala Leu Lys Ile Ala Phe Gly Phe Asn Glu Pro Asn Gly Asn Leu Gln
    530                 535                 540

Tyr Gln Gly Lys Asp Ile Thr Glu Phe Asp Phe Asn Phe Asp Gln Gln
545                 550                 555                 560

Thr Ser Gln Asn Ile Lys Asn Gln Leu Ala Glu Leu Asn Ala Thr Asn
                565                 570                 575

Ile Tyr Thr Val Leu Asp Lys Ile Lys Leu Asn Ala Lys Met Asn Ile
            580                 585                 590

Leu Ile Arg Asp Lys Arg Phe His Tyr Asp Arg Asn Asn Ile Ala Val
        595                 600                 605

Gly Ala Asp Glu Ser Val Val Lys Glu Ala His Arg Glu Val Ile Asn
    610                 615                 620

Ser Ser Thr Glu Gly Leu Leu Leu Asn Ile Asp Lys Asp Ile Arg Lys
625                 630                 635                 640

Ile Leu Ser Gly Tyr Ile Val Glu Ile Glu Asp Thr Glu Gly Leu Lys
```

-continued

Glu Val Ile Asn Asp Arg Tyr Asp Met Leu Asn Ile Ser Ser Leu Arg
            645                 650                 655
Gln Asp Gly Lys Thr Phe Ile Asp Phe Lys Lys Tyr Asn Asp Lys Leu
660                 665                 670
        675                 680                 685
Pro Leu Tyr Ile Ser Asn Pro Asn Tyr Lys Val Asn Val Tyr Ala Val
        690                 695                 700
Thr Lys Glu Asn Thr Ile Ile Asn Pro Ser Glu Asn Gly Asp Thr Ser
705                 710                 715                 720
Thr Asn Gly Ile Lys Lys Ile Leu Ile Phe Ser Lys Lys Gly Tyr Glu
                725                 730                 735
Ile Gly

<210> SEQ ID NO 12
<211> LENGTH: 738
<212> TYPE: PRT
<213> ORGANISM: Artificial
<220> FEATURE:
<223> OTHER INFORMATION: PrAg-U4 cleavable by tPA

<400> SEQUENCE: 12

Glu Val Lys Gln Glu Asn Arg Leu Leu Asn Glu Ser Glu Ser Ser Ser
1               5                   10                  15
Gln Gly Leu Leu Gly Tyr Tyr Phe Ser Asp Leu Asn Phe Gln Ala Pro
                20                  25                  30
Met Val Val Thr Ser Ser Thr Thr Gly Asp Leu Ser Ile Pro Ser Ser
            35                  40                  45
Glu Leu Glu Asn Ile Pro Ser Glu Asn Gln Tyr Phe Gln Ser Ala Ile
50                  55                  60
Trp Ser Gly Phe Ile Lys Val Lys Lys Ser Asp Glu Tyr Thr Phe Ala
65                  70                  75                  80
Thr Ser Ala Asp Asn His Val Thr Met Trp Val Asp Asp Gln Glu Val
                85                  90                  95
Ile Asn Lys Ala Ser Asn Ser Asn Lys Ile Arg Leu Glu Lys Gly Arg
            100                 105                 110
Leu Tyr Gln Ile Lys Ile Gln Tyr Gln Arg Glu Asn Pro Thr Glu Lys
        115                 120                 125
Gly Leu Asp Phe Lys Leu Tyr Trp Thr Asp Ser Gln Asn Lys Lys Glu
    130                 135                 140
Val Ile Ser Ser Asp Asn Leu Gln Leu Pro Glu Leu Lys Gln Lys Ser
145                 150                 155                 160
Ser Asn Ser Pro Gln Arg Gly Arg Ser Ala Ser Thr Ser Ala Gly Pro
                165                 170                 175
Thr Val Pro Asp Arg Asp Asn Asp Gly Ile Pro Asp Ser Leu Glu Val
            180                 185                 190
Glu Gly Tyr Thr Val Asp Val Lys Asn Lys Arg Thr Phe Leu Ser Pro
        195                 200                 205
Trp Ile Ser Asn Ile His Glu Lys Lys Gly Leu Thr Lys Tyr Lys Ser
    210                 215                 220
Ser Pro Glu Lys Trp Ser Thr Ala Ser Asp Pro Tyr Ser Asp Phe Glu
225                 230                 235                 240
Lys Val Thr Gly Arg Ile Asp Lys Asn Val Ser Pro Glu Ala Arg His
                245                 250                 255
Pro Leu Val Ala Ala Tyr Pro Ile Val His Val Asp Met Glu Asn Ile
            260                 265                 270

```
Ile Leu Ser Lys Asn Glu Asp Gln Ser Thr Gln Asn Thr Asp Ser Glu
        275                 280                 285

Thr Arg Thr Ile Ser Lys Asn Thr Ser Thr Ser Arg Thr His Thr Ser
        290                 295                 300

Glu Val His Gly Asn Ala Glu Val His Ala Ser Phe Phe Asp Ile Gly
305                 310                 315                 320

Gly Ser Val Ser Ala Gly Phe Ser Asn Ser Asn Ser Ser Thr Val Ala
                325                 330                 335

Ile Asp His Ser Leu Ser Leu Ala Gly Glu Arg Thr Trp Ala Glu Thr
                340                 345                 350

Met Gly Leu Asn Thr Ala Asp Thr Ala Arg Leu Asn Ala Asn Ile Arg
        355                 360                 365

Tyr Val Asn Thr Gly Thr Ala Pro Ile Tyr Asn Val Leu Pro Thr Thr
        370                 375                 380

Ser Leu Val Leu Gly Lys Asn Gln Thr Leu Ala Thr Ile Lys Ala Lys
385                 390                 395                 400

Glu Asn Gln Leu Ser Gln Ile Leu Ala Pro Asn Asn Tyr Tyr Pro Ser
                405                 410                 415

Lys Asn Leu Ala Pro Ile Ala Leu Asn Ala Gln Asp Asp Phe Ser Ser
                420                 425                 430

Thr Pro Ile Thr Met Asn Tyr Asn Gln Phe Leu Glu Leu Glu Lys Thr
        435                 440                 445

Lys Gln Leu Arg Leu Asp Thr Asp Gln Val Tyr Gly Asn Ile Ala Thr
        450                 455                 460

Tyr Asn Phe Glu Asn Gly Arg Val Arg Val Asp Thr Gly Ser Asn Trp
465                 470                 475                 480

Ser Glu Val Leu Pro Gln Ile Gln Glu Thr Thr Ala Arg Ile Ile Phe
                485                 490                 495

Asn Gly Lys Asp Leu Asn Leu Val Glu Arg Arg Ile Ala Ala Val Asn
                500                 505                 510

Pro Ser Asp Pro Leu Glu Thr Thr Lys Pro Asp Met Thr Leu Lys Glu
        515                 520                 525

Ala Leu Lys Ile Ala Phe Gly Phe Asn Glu Pro Asn Gly Asn Leu Gln
        530                 535                 540

Tyr Gln Gly Lys Asp Ile Thr Glu Phe Asp Phe Asn Phe Asp Gln Gln
545                 550                 555                 560

Thr Ser Gln Asn Ile Lys Asn Gln Leu Ala Glu Leu Asn Ala Thr Asn
                565                 570                 575

Ile Tyr Thr Val Leu Asp Lys Ile Lys Leu Asn Ala Lys Met Asn Ile
                580                 585                 590

Leu Ile Arg Asp Lys Arg Phe His Tyr Asp Arg Asn Asn Ile Ala Val
        595                 600                 605

Gly Ala Asp Glu Ser Val Val Lys Glu Ala His Arg Glu Val Ile Asn
        610                 615                 620

Ser Ser Thr Glu Gly Leu Leu Leu Asn Ile Asp Lys Asp Ile Arg Lys
625                 630                 635                 640

Ile Leu Ser Gly Tyr Ile Val Glu Ile Glu Asp Thr Glu Gly Leu Lys
                645                 650                 655

Glu Val Ile Asn Asp Arg Tyr Asp Met Leu Asn Ile Ser Ser Leu Arg
                660                 665                 670

Gln Asp Gly Lys Thr Phe Ile Asp Phe Lys Lys Tyr Asn Asp Lys Leu
        675                 680                 685
```

```
Pro Leu Tyr Ile Ser Asn Pro Asn Tyr Lys Val Asn Val Tyr Ala Val
        690             695                 700

Thr Lys Glu Asn Thr Ile Ile Asn Pro Ser Glu Asn Gly Asp Thr Ser
705             710                 715                 720

Thr Asn Gly Ile Lys Lys Ile Leu Ile Phe Ser Lys Lys Gly Tyr Glu
                725                 730                 735

Ile Gly

<210> SEQ ID NO 13
<211> LENGTH: 590
<212> TYPE: PRT
<213> ORGANISM: Artificial
<220> FEATURE:
<223> OTHER INFORMATION: amino acids 175-764 of PA

<400> SEQUENCE: 13

Ile Ser Ser Asp Asn Leu Gln Leu Pro Glu Leu Lys Gln Lys Ser Ser
1               5                   10                  15

Asn Ser Arg Lys Lys Arg Ser Thr Ser Ala Gly Pro Thr Val Pro Asp
                20                  25                  30

Arg Asp Asn Asp Gly Ile Pro Asp Ser Leu Glu Val Glu Gly Tyr Thr
            35                  40                  45

Val Asp Val Lys Asn Lys Arg Thr Phe Leu Ser Pro Trp Ile Ser Asn
50                  55                  60

Ile His Glu Lys Lys Gly Leu Thr Lys Tyr Lys Ser Ser Pro Glu Lys
65                  70                  75                  80

Trp Ser Thr Ala Ser Asp Pro Tyr Ser Asp Phe Glu Lys Val Thr Gly
                85                  90                  95

Arg Ile Asp Lys Asn Val Ser Pro Glu Ala Arg His Pro Leu Val Ala
            100                 105                 110

Ala Tyr Pro Ile Val His Val Asp Met Glu Asn Ile Ile Leu Ser Lys
        115                 120                 125

Asn Glu Asp Gln Ser Thr Gln Asn Thr Asp Ser Glu Thr Arg Thr Ile
130                 135                 140

Ser Lys Asn Thr Ser Thr Ser Arg Thr His Thr Ser Glu Val His Gly
145                 150                 155                 160

Asn Ala Glu Val His Ala Ser Phe Phe Asp Ile Gly Gly Ser Val Ser
                165                 170                 175

Ala Gly Phe Ser Asn Ser Asn Ser Ser Thr Val Ala Ile Asp His Ser
            180                 185                 190

Leu Ser Leu Ala Gly Glu Arg Thr Trp Ala Glu Thr Met Gly Leu Asn
        195                 200                 205

Thr Ala Asp Thr Ala Arg Leu Asn Ala Asn Ile Arg Tyr Val Asn Thr
210                 215                 220

Gly Thr Ala Pro Ile Tyr Asn Val Leu Pro Thr Thr Ser Leu Val Leu
225                 230                 235                 240

Gly Lys Asn Gln Thr Leu Ala Thr Ile Lys Ala Lys Glu Asn Gln Leu
                245                 250                 255

Ser Gln Ile Leu Ala Pro Asn Asn Tyr Tyr Pro Ser Lys Asn Leu Ala
            260                 265                 270

Pro Ile Ala Leu Asn Ala Gln Asp Asp Phe Ser Ser Thr Pro Ile Thr
        275                 280                 285

Met Asn Tyr Asn Gln Phe Leu Glu Leu Glu Lys Thr Lys Gln Leu Arg
    290                 295                 300

Leu Asp Thr Asp Gln Val Tyr Gly Asn Ile Ala Thr Tyr Asn Phe Glu
```

-continued

```
            305                 310                 315                 320
    Asn Gly Arg Val Arg Val Asp Thr Gly Ser Asn Trp Ser Glu Val Leu
                    325                 330                 335

Pro Gln Ile Gln Glu Thr Thr Ala Arg Ile Ile Phe Asn Gly Lys Asp
                    340                 345                 350

Leu Asn Leu Val Glu Arg Arg Ile Ala Ala Val Asn Pro Ser Asp Pro
                    355                 360                 365

Leu Glu Thr Thr Lys Pro Asp Met Thr Leu Lys Glu Ala Leu Lys Ile
                    370                 375                 380

Ala Phe Gly Phe Asn Glu Pro Asn Gly Asn Leu Gln Tyr Gln Gly Lys
    385                 390                 395                 400

Asp Ile Thr Glu Phe Asp Phe Asn Phe Asp Gln Gln Thr Ser Gln Asn
                    405                 410                 415

Ile Lys Asn Gln Leu Ala Glu Leu Asn Ala Thr Asn Ile Tyr Thr Val
                    420                 425                 430

Leu Asp Lys Ile Lys Leu Asn Ala Lys Met Asn Ile Leu Ile Arg Asp
                    435                 440                 445

Lys Arg Phe His Tyr Asp Arg Asn Asn Ile Ala Val Gly Ala Asp Glu
                    450                 455                 460

Ser Val Val Lys Glu Ala His Arg Glu Val Ile Asn Ser Ser Thr Glu
    465                 470                 475                 480

Gly Leu Leu Leu Asn Ile Asp Lys Asp Ile Arg Lys Ile Leu Ser Gly
                    485                 490                 495

Tyr Ile Val Glu Ile Glu Asp Thr Glu Gly Leu Lys Glu Val Ile Asn
                    500                 505                 510

Asp Arg Tyr Asp Met Leu Asn Ile Ser Ser Leu Arg Gln Asp Gly Lys
                    515                 520                 525

Thr Phe Ile Asp Phe Lys Lys Tyr Asn Asp Lys Leu Pro Leu Tyr Ile
                    530                 535                 540

Ser Asn Pro Asn Tyr Lys Val Asn Val Tyr Ala Val Thr Lys Glu Asn
    545                 550                 555                 560

Thr Ile Ile Asn Pro Ser Glu Asn Gly Asp Thr Ser Thr Asn Gly Ile
                    565                 570                 575

Lys Lys Ile Leu Ile Phe Ser Lys Lys Gly Tyr Glu Ile Gly
                    580                 585                 590

<210> SEQ ID NO 14
<211> LENGTH: 4
<212> TYPE: PRT
<213> ORGANISM: Bacillus anthracis

<400> SEQUENCE: 14

Arg Lys Lys Arg
1

<210> SEQ ID NO 15
<211> LENGTH: 4
<212> TYPE: PRT
<213> ORGANISM: Artificial
<220> FEATURE:
<223> OTHER INFORMATION: SNKE mutation

<400> SEQUENCE: 15

Ser Asn Lys Glu
1
```

METHODS FOR PREPARING *BACILLUS ANTHRACIS* PROTECTIVE ANTIGEN FOR USE IN VACCINES

CROSS REFERENCE TO RELATED APPLICATION

This application claims the benefit of U.S. Provisional Application No. 60/344,505 filed Nov. 9, 2001.

FIELD OF THE INVENTION

This invention relates to improved methods of preparing *Bacillus anthracis* protective antigen (PA) for use in vaccines.

BACKGROUND

Anthrax, a potentially fatal disease, is caused by *Bacillus anthracis*. The virulence of this pathogen is mediated by a capsule of a poly-D-γ-glutamic acid and an exotoxin composed of three proteins (14, 16, 17). The three protein components are the protective antigen (PA, 82 KDa), lethal factor (LF, 90.2 KDa) and edema factor (EF, 88.8 KDa) These proteins, non-toxic by themselves, form lethal toxins when combined with an activated PA (16). The genes coding for these three protein components and the capsule are found in the endogenous plasmids pXO1 and pXO2, respectively (29).

The capsule of *Bacillus anthracis*, composed of poly-D-glutamic acid, serves as one of the principal virulence factors during anthrax infection. By virtue of its negative charge, the capsule is purported to inhibit host defence through inhibition of phagocytosis of the vegetative cells by macrophages. In conjunction with lethal factor (LF) and edema factor (EF), whose target cells include macrophages and neutrophils, respectively, the capsule allows virulent anthrax bacilli to grow virtually unimpeded in the infected host. Spores germinating in the presence of serum and elevated $CO_2$ release capsule through openings on the spore surface in the form of blebs which may coalesce before sloughing of the exosporium and outgrowth of the fully encapsulated vegetative cell. It has not been established that spore encapsulation plays a role in the early events of anthrax infection. The capsule appears exterior to the S-layer of the vegetative cell and does not require the S-layer for its attachment to the cell surface.

There is only indirect evidence, albeit extensive, identifying the components of vaccine-induced immunity to anthrax and there is evidence that anti-PA neutralizing antibody titers can be a reliable surrogate marker for protective immunity (23). The protective antigen (PA), seems to be an essential component of all vaccines for anthrax (7, 18, 30): both mono and polyclonal antibodies to PA neutralize the anthrax toxin and confer immunity to *B. antrhacis* in animal models. The US licensed vaccine for anthrax "Anthrax Vaccine Adsorbed" (AVA) is produced from the formalin-treated culture supernatant of *B. anthracis* Sterne strain, V770-NP1-R (pXO1$^+$, pXO2$^-$), adsorbed onto aluminum hydroxide (22). Although AVA has been shown to be effective against cutaneous infection in animals and humans and against inhalation anthrax by rhesus monkeys (12), it has several limitations: 1) AVA elicits relatively high degree of local and systemic adverse reactions probably mediated by variable amounts of undefined bacterial products, making standardization difficult; 2) the immunization schedule requires administration of six doses within an eighteen-month period, followed by annual boosters for those at risk; and 3) there is no defined vaccine-induced protective level of serum PA to evaluate new lots of vaccines.

Development of a well characterized, standardized, effective and safe vaccine that would require fewer doses to confer immunity to both inhalational and cutaneous anthrax is needed (9, 30). It has been suggested that a vaccine composed of modified purified recombinant PA would be effective, safer, allow precise standardization, and probably would require fewer injections (27). Such a PA can be designed to be biologically inactive, more stable, and still maintained high immunogenicity.

In the examples herein, we describe the development of a production and purification process for recombinant PA from the non-sporogenic avirulent *B. anthracis* BH445 (pXO1$^-$, pXO2$^-$) strain. Following an 18-hour fermentation and three purification steps, large quantities of protective antigen suitable for vaccine production were obtained. The purified PA was tested in mice and was able to elicit neutralizing antibodies.

BRIEF DESCRIPTION OF THE INVENTION

This invention relates to improved methods of preparing *Bacillus anthracis* protective antigen (PA).

The invention also relates to PA and/or compositions thereof, which are useful for inducing or eliciting an immunogenic response in mammals, including responses which provide protection against, or reduce the severity of, infections caused by *B. anthracis*. In particular, the invention relates to methods of using PA, and/or compositions thereof, to induce or elicit serum antibodies which have neutralizing activity against *B. anthracis* toxin. PA and/or compositions thereof are useful as vaccines to induce serum antibodies which are useful to prevent, treat or reduce the severity of infections caused by *B. anthracis*, such as inhalation anthrax, cutaneous anthrax and/or gastrointestinal anthrax.

The invention also relates to nucleic acids encoding PA of *B. anthracis*, and compositions thereof, which produce PA in sufficient amounts to be useful as pharmaceutical compositions or vaccines to induce serum antibodies for preventing and/or treating illnesses caused by *B. anthracis*. The invention also relates to suitable expression systems, viral particles, vectors, vector systems, and transformed host cells containing those nucleic acids.

The invention also relates to antibodies which immunoreact with the PA of *B. anthracis*, and/or compositions thereof. Such antibodies may be isolated, or may be provided in the form of serum containing these antibodies.

The invention also relates to pharmaceutical compositions and/or vaccines comprising at least one of the PAs, nucleic acids, viral particles, vectors, vector systems, transformed host cells or antibodies of the invention.

The invention also relates to methods for the prevention or treatment of *B. anthracis* infection in a mammal, by administration of pharmaceutical or vaccine compositions of the invention.

The invention also provides kits comprising one or more of the agents of the invention which are useful for vaccinating mammals for the treatment or prevention of *B. anthracis* infection.

BRIEF DESCRIPTION OF THE DRAWINGS

FIG. 1. Production and proteolytic activity of PA-SNKE-ΔFF-E308D and PA-N657A. (a) PA production (mg/g cells) ● SNKE, ■ N657A; proteolytic activity ○ SNKE, □ N657A; (b) SDS-PAGE analysis of partially purified PA-N657A and PA-SNKE-ΔFF-E308D.

FIG. 2. Effect of EDTA and PMSF on proteolytic activity. Supernatants from two different cultures taken after 24 hours of growth were analyzed without inhibitors (control), with 1 μg/μL PMSF, and with 15 mM EDTA. Fluorescence is proportional to proteolytic activity.

DETAILED DESCRIPTION OF THE INVENTION

Figure 3:
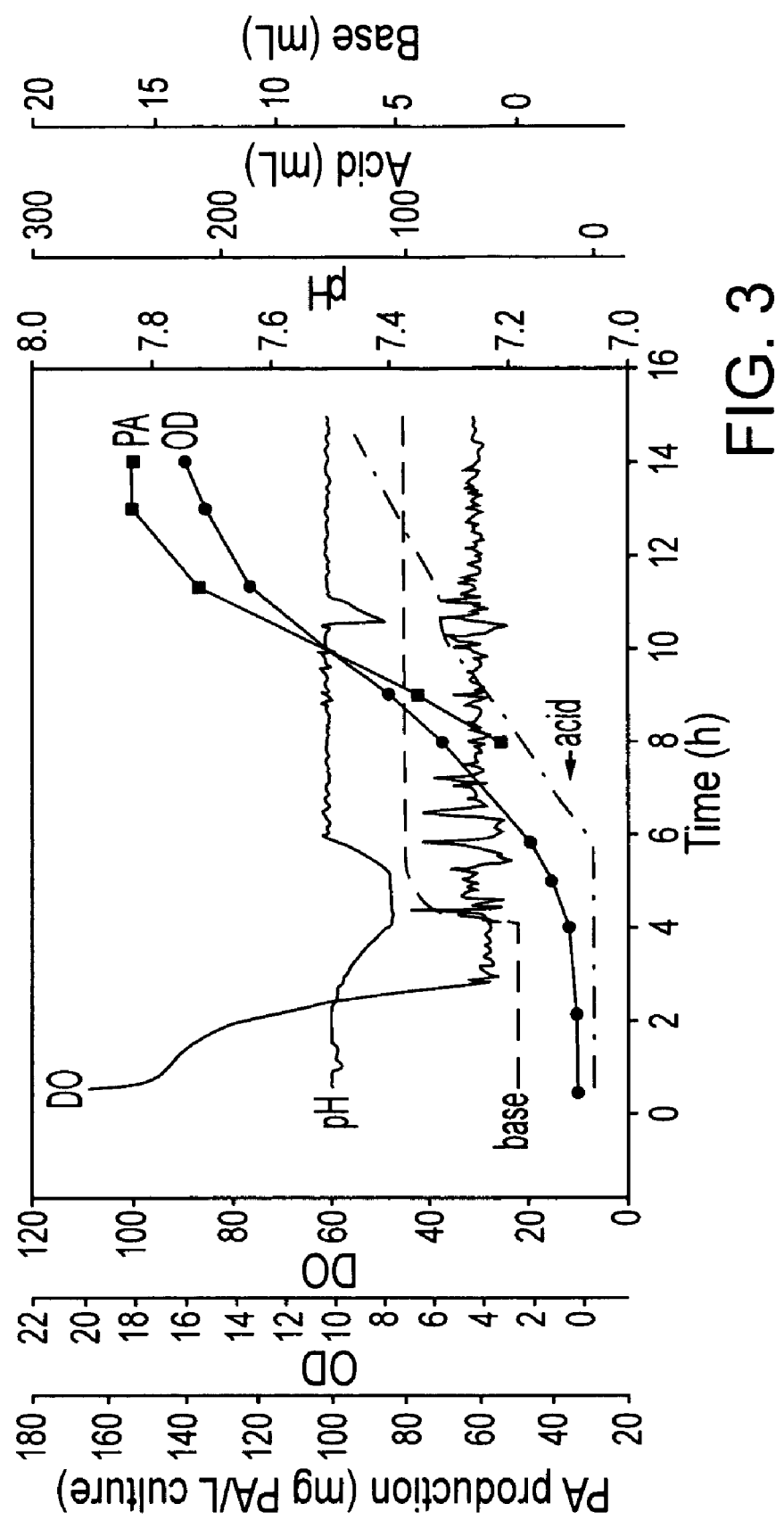
FIG. 3. Fermentation process for the production of PA-SNKE-ΔFF-E308D from *B. anthracis* BH445. Acid and base values are cumulative.

It is to be understood that both the foregoing general description and the following detailed description are exemplary and explanatory only, and are not restrictive of the invention, as claimed. The accompanying drawings, which are incorporated in and constitute a part of the specification, illustrate an embodiment of the invention and, together with the description, serve to explain the principles of the invention.

The invention relates to methods of producing and recovering PA from a cell or organism, particularly a recombinant cell or microorganism. Exemplified herein is the production and purification of modified PA from a non-sporgenic strain of *Bacillus anthracis*. As discussed further herein, greater quantities of PA are obtainable from these cells or microorganisms than were obtainable by previously described methods.

The invention also relates to PA, and/or compositions thereof, which are useful for eliciting an immunogenic response in mammals, in particular humans, including responses which provide protection against, or reduce the severity of, infections caused by *B. anthracis*. The invention also relates to methods of using such PA, and/or compositions thereof, to induce serum antibodies against PA. PA, and/or compositions thereof, are useful as vaccines to induce serum antibodies which are useful to prevent, treat or reduce the severity of infections caused by *B. anthracis*, such as inhalation anthrax and/or cutaneous anthrax. The PAs of this invention are expected to induce a strong protective IgG antibody response in mammals, including humans.

The invention also relates to nucleic acids encoding PA of this invention. Nucleic acids encoding PA, and compositions thereof, are also useful as pharmaceutical compositions or vaccines to induce serum antibodies which are useful to prevent and/or treat illnesses caused by *B. anthracis*.

The invention also relates to antibodies which immunoreact with the PA of *B. anthracis* that are induced by PAs of the invention, and/or compositions thereof. Such antibodies may be isolated, or may be provided in the form of serum containing these antibodies.

The invention also relates to a method for the prevention or treatment of *B. anthracis* infection in a mammal, by administration of compositions containing one or more of a PA of the invention, nucleic acids encoding a PA if the invention, antibodies and/or serum containing antibodies of the invention.

The invention also provides kits for vaccinating mammals for the treatment or prevention of *B. anthracis* infection in a mammal comprising one or more of the agents of the invention.

The present invention also encompasses methods of using mixtures of one or more of the PA, nucleic acids, and/or antibodies of the invention, either in a single composition or in multiple compositions containing other immunogens, to form a multivalent vaccine for broad coverage against either *B. anthracis* itself or a combination of *B. anthracis* and one or more other pathogens, which may also be administered concurrently with other vaccines, such as the DTP vaccine.

Pharmaceutical compositions of this invention are capable, upon injection into a human, of inducing serum antibodies against *B. anthracis*. The induced anti-PA antibodies have anthrax toxin neutralizing activity which are preferably at least comparable to those induced by the currently licensed anthrax vaccine.

The vaccines of this invention are intended for active immunization for prevention of *B. anthracis* infection, and for preparation of immune antibodies. The vaccines of this invention are designed to confer specific immunity against infection with *B. anthracis*, and to induce antibodies specific to *B. anthracis* PA. The B. anthracis vaccine is composed of non-toxic bacterial components, suitable for infants, children of all ages, and adults.

The methods of using the agents of this invention, and/or compositions thereof will be useful in increasing resistance to, preventing, ameliorating, and/or treating *B. anthracis* infection in humans.

This invention also provides compositions, including but not limited to, mammalian serum, plasma, and immunoglobulin fractions, which contain antibodies which are immunoreactive with *B. anthracis* PA. These antibodies and antibody compositions may be useful to prevent, treat, and/or ameliorate infection and disease caused by the microorganism. The invention also provides such antibodies in isolated form.

High titer anti-PA sera, or antibodies isolated therefrom, may be used for therapeutic treatment for patients with *B. anthracis* infection. Antibodies elicited by the agents of this invention may be used for the treatment of established B. anthracis infections, and may also be useful in providing passive protection to an individual exposed to *B. anthracis*.

The present invention also provides kits comprising vaccines for the prevention and/or treatment of *B. anthracis*, containing the one or more of the PAs, nucleic acids, viral particles, vectors, vector systems, or transformed host cells or antibodies of the invention and/or compositions thereof. The PAs, nucleic acids viral particles vectors, host cells and/or antibodies of the present invention may be isolated and purified by methods known in the art. Preferably, the PA of the invention is purified by one of the methods exemplified herein.

The vaccines of the invention are intended to be included in the immunization schedule of individuals at risk for *B. anthracis* infection. They are also planned to be used for intervention in the event of the use of *B. anthracis* in bioterrorism or biowarfare. For example, it is anticipated that the vaccines of the invention may be provided to the entire U.S. population. Additionally, they may be used as component(s) of a multivalent vaccine for *B. anthracis* and/or other pathogens.

Definitions

As used herein, unless otherwise specifically noted, "PA" refers to all forms of PA which are useful in the compositions and/or methods of the invention, including unmodified native or recombinant *B. anthracis* protective antigen (PA), or a modified form (variant) or fragment thereof, for use in vaccines. Variants and fragments of PA must be able to produce an immune response in a mammal to whom they are administered. The immune response is suitably protective against infection by *Bacillus anthracis* although the protective effect may be seen only after repeated applications, as would be determinable by methods known in the art. Modified PA variants comprise peptides and proteins which resemble PA in their ability to induce or elicit antibodies which bind to native PA, but have different amino acid sequence. For example, variants may be 60% homologous to PA protein, suitably 80% homologous and more particularly at least 90% homologous. Fragments are suitably peptides which contain at least one antigenic determinant of PA.

A modified (variant) PA of the invention includes any substituted analog or chemical derivative of PA, so long as the modified (variant) PA is capable of inducing or eliciting the production of antibodies capable of binding native (or naturally-occurring) PA. Preferably, the antibodies are neutralizing antibodies. PA can be subject to various changes that provide for certain advantages in its use. For example, PA with changes which increase in vitro and/or in vivo stability of PA, while still retaining the desired immunogenic activity, are preferred. In the modified PA used in the examples herein, two regions were altered, i.e., the furin cleavage site region (RKKR167 [SEQ ID NO: 14] to SNKE167 [SEQ ID NO: 15]), and the chymotrypsin and thermolysin cleavage site region (two Phe at positions 313-314 were deleted and Glu acid at position 308 was substituted with Asp), resulting in a more stable PA. As used herein, the terms "immunoreact" and "immunoreactivity" refer to specific binding between an antigen or antigenic determinant-containing molecule and a molecule having an antibody combining site, such as a whole antibody molecule or a portion thereof.

As used herein, the term "antibody" refers to immunoglobulin molecules and immunologically active portions of immunoglobulin molecules. Exemplary antibody molecules are intact immunoglobulin molecules, substantially intact immunoglobulin molecules and portions of an immunoglobulin molecule, including those portions known in the art as Fab, Fab', F(ab')$_2$ and F(v), as well as chimeric antibody molecules.

As used herein, the term "transduction" generally refers to the transfer of genetic material into the host via infection, e.g., in this case by the lentiviral vector. The term "transfection" generally refers to the transfer of isolated genetic material into cells via the use of specific transfection agents (e.g., calcium phosphate, DEAE Dextran, lipid formulations, gold particles, and other microparticles) that cross the cytoplasmic membrane and deliver some of the genetic material into the cell nucleus.

Monomers, Polymers and Polymeric Carriers

The present invention encompasses monomers of PA, as well as homogeneous or heterogeneous polymers of PA (e.g., concatenated, cross-linked and/or fused identical polypeptide units or concatenated, cross-linked and/or fused diverse peptide units), and mixtures of the polypeptides, polymers, and/or conjugates thereof. The present invention also encompasses PA bound to a non-toxic, preferably non-host, protein carrier to form a conjugate.

Linkers useful in the invention may, for example, be simply peptide bonds, or may comprise amino acids, including amino acids capable of forming disulfide bonds, but may also comprise other molecules such as, for example, polysaccharides or fragments thereof.

The linkers for use with this invention may be chosen so as to contribute their own immunogenic effect which may be either the same, or different, than that elicited by the consensus sequences of the invention. For example, such linkers may be bacterial antigens which also elicit the production of antibodies to infectious bacteria. In such instances, for example, the linker may be a protein or protein fragment of an infectious bacteria.

Carriers are chosen to increase the immunogenicity of the PA and/or to raise antibodies against the carrier which are medically beneficial. Carriers that fulfill these criteria are well known in the art. A polymeric carrier can be a natural or a synthetic material containing one or more functional groups, for example primary and/or secondary amino groups, azido groups, or carboxyl groups. Carriers can be water soluble or insoluble.

Methods for Attaching PA to a Protein Carrier.

PA of the invention may be covalently attached to other proteins, with or without a linker, by methods known in the art, such as via their side chains or via peptide bonds in the primary chain. Cysteine molecules may provide a convenient attachment point through which to chemically conjugate other proteins or non-protein moieties to PA.

Dosage for Vaccination

The pharmaceutical compositions of this invention contain a pharmaceutically and/or therapeutically effective amount of at least one PA, nucleic acid, vector, viral particle, host cell immunogen or antibody of the invention. The effective amount of immunogen per unit dose is an amount sufficient to induce an immune response which is sufficient to prevent, treat or protect against the adverse effects of infection with *B. anthracis*. The effective amount of immunogen per unit dose depends, among other things, on the species of mammal inoculated, the body weight of the mammal and the chosen inoculation regimen, as is well known in the art.

In such circumstances, inocula for a human or similarly sized mammal typically contain PA concentrations of 0.5 µg to I mg per mammal per inoculation dose. Initial tests of the PA vaccine in humans will use approximately 10 µg or 20 µg per dose. Preferably, the route of inoculation of the peptide will be subcutaneous or intramuscular. The dose is administered at least once.

To monitor the antibody response of individuals administered the compositions of the invention, antibody levels may be determined. In most instances it will be sufficient to assess the antibody titer in serum or plasma obtained from such an individual. Decisions as to whether to administer booster inoculations or to change the amount of the composition administered to the individual may be at least partially based on the level.

The level may be based on either an immunobinding assay which measures the concentration of antibodies in the serum which bind to a specific antigen, i.e. PA. The ability to neutralize in vitro and in vivo biological effects of the *B. anthracis* toxins may also be assessed to determine the effectiveness of the treatment.

The term "unit dose" as it pertains to the inocula refers to physically discrete units suitable as unitary dosages for mammals, each unit containing a predetermined quantity of active material calculated to produce the desired immunogenic effect in association with the required diluent.

Inocula are typically prepared in physiologically and/or pharmaceutically tolerable (acceptable) carrier, and are preferably prepared as solutions in physiologically and/or pharmaceutically acceptable diluents such as water, saline, phosphate-buffered saline, or the like, to form an aqueous pharmaceutical composition. Adjuvants, such as aluminum hydroxide, may also be included in the compositions.

Depending on the intended mode of administration, the compounds of the present invention can be in various pharmaceutical compositions. The compositions will include, as noted above, an effective amount of the selected immunogen and/or antibody of the invention in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the immunogen and/or antibody or other composition without causing any undesirable biological effects or interacting in a deleterious manner with any of the other components of the pharmaceutical composition in which it is contained.

The route of inoculation may be intramuscular, subcutaneous or the like, which results in eliciting antibodies protective against B. anthracis. In order to increase the antibody level, a second or booster dose may be administered approximately 4 to 6 weeks after the initial injection. Subsequent doses may be administered as indicated herein, or as desired by the practitioner.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

Antibodies

An antibody of the present invention in one embodiment is characterized as comprising antibody molecules that immunoreact with B. anthracis PA.

An antibody of the present invention is typically produced by immunizing a mammal with an immunogen or vaccine containing an B. anthracis PA to induce, in the mammal, antibody molecules having immunospecificity for the immunizing PA. Antibody molecules having immunospecificity for the protein carrier will also be produced. The antibody molecules may be collected from the mammal and, optionally, isolated and purified by methods known in the art.

Human or humanized monoclonal antibodies are preferred, including those made by phage display technology, by hybridomas, or by mice with human immune systems. The antibody molecules of the present invention may be polyclonal or monoclonal. Monoclonal antibodies may be produced by methods known in the art. Portions of immunoglobulin molecules, such as Fabs, may also be produced by methods known in the art.

The antibody of the present invention may be contained in blood plasma, serum, hybridoma supernatants and the like. Alternatively, the antibodies of the present invention are isolated to the extent desired by well known techniques such as, for example, ion exchange chromatography, sizing chromatography, or affinity chromatography. The antibodies may be purified so as to obtain specific classes or subclasses of antibody such as IgM, IgG, IgA, $IgG_1$, $IgG_2$, $IgG_3$, $IgG_4$ and the like. Antibodies of the IgG class are preferred for purposes of passive protection. The antibodies of the present invention have a number of diagnostic and therapeutic uses. The antibodies can be used as an in vitro diagnostic agents to test for the presence of B. anthracis in biological samples or in meat and meat products, in standard immunoassay protocols. Such assays include, but are not limited to, agglutination assays, radioimmunoassays, enzyme-linked immunosorbent assays, fluorescence assays, Western blots and the like. In one such assay, for example, the biological sample is contacted first with antibodies of the present invention which bind to B. anthracis PA, and then with a labeled second antibody to detect the presence of B. anthracis to which the first antibodies have bound.

Such assays may be, for example, of direct format (where the labeled first antibody is reactive with the antigen), an indirect format (where a labeled second antibody is reactive with the first antibody), a competitive format (such as the addition of a labeled antigen), or a sandwich format (where both labeled and unlabelled antibody are utilized), as well as other formats described in the art.

The antibodies of the present invention are also useful in prevention and treatment of infections and diseases caused by B. anthracis.

In providing the antibodies of the present invention to a recipient mammal, preferably a human, the dosage of administered antibodies will vary depending upon such factors as the mammal's age, weight, height, sex, general medical condition, previous medical history and the like.

In general, it is desirable to provide the recipient with a dosage of antibodies which is in the range of from about 1 mg/kg to about 10 mg/kg body weight of the mammal, although a lower or higher dose may be administered. The antibodies of the present invention are intended to be provided to the recipient subject in an amount sufficient to prevent, or lessen or attenuate the severity, extent or duration of the infection by B. anthracis. When proteins of other organisms are used as carriers, antibodies which immunoreact with those proteins are intended to be provided to the recipient subject in an amount sufficient to prevent, lessen or attenuate the severity, extent or duration of an infection by the organisms producing those proteins.

The administration of the agents of the invention may be for either "prophylactic" or "therapeutic" purpose. When provided prophylactically, the agents are provided in advance of any symptom. The prophylactic administration of the agent serves to prevent or ameliorate any subsequent infection. When provided therapeutically, the agent is provided at (or shortly after) the onset of a symptom of infection. The agent of the present invention may, thus, be provided prior to the anticipated exposure to B. anthracis, so as to attenuate the anticipated severity, duration or extent of an infection and disease symptoms, after exposure or suspected exposure to these bacteria, or after the actual initiation of an infection.

For all therapeutic, prophylactic and diagnostic uses, one or more of the PAs or other agents of this invention, as well as antibodies and other necessary reagents and appropriate devices and accessories, may be provided in kit form so as to be readily available and easily used.

Nucleic Acids, Vectors and Hosts

The invention also relates to isolated and purified nucleic acid molecules which code for the PAs of the invention. The encoded PAs may be monomers, polymers or linked to other peptide sequences (e.g., they may be fusion proteins).

Nucleic acids encoding the PAs of the invention can be introduced into a vector such as a plasmid, cosmid, phage, virus, viral particle or mini-chromosome and inserted into a host cell or organism by methods well known in the art. The vectors which can be utilized to clone and/or express these nucleic acids are the vectors which are capable of replicating and/or expressing the nucleic acids in the host cell in which the nucleic acids are desired to be replicated and/or expressed. See, e.g., F. Ausubel et al., Current Protocols in Molecular Biology, Greene Publishing Associates and Wiley-Interscience (1992) and Sambrook et al. (1989) for examples of appropriate vectors for various types of host cells. Vectors and compositions for enabling production of the peptides in vivo, i.e., in the individual to be treated or immunized, are also within the scope of this invention. Strong promoters compatible with the host into which the gene is inserted may be used. These promoters may be inducible. The host cells containing these nucleic acids can be used to express large amounts of the protein useful in pharmaceuticals, diagnostic reagents, vaccines and therapeutics. Vectors include retroviral vectors and also include direct injection of DNA into muscle cells or other receptive cells, resulting in the efficient expression of the peptide, using the technology described, for example, in Wolff et al., Science 247:1465-1468 (1990), Wolff et al., Human Molecular Genetics 1(6):363-369 (1992) and Ulmer et al., Science 259:1745-1749 (1993). See also, for example, WO 96/36366 and WO 98/34640.

In general, vectors containing nucleic acids encoding PA can be utilized in any cell, either eukaryotic or prokaryotic, including mammalian cells (e.g., human (e.g., HeLa), monkey (e.g., COS), rabbit (e.g., rabbit reticulocytes), rat, hamster (e.g., CHO and baby hamster kidney cells) or mouse cells (e.g., L cells), plant cells, yeast cells, insect cells or bacterial cells (e.g., E. coli). However, bacterial vectors and host cells are preferred in the present invention.

There are numerous E. coli expression vectors known to one of ordinary skill in the art useful for the expression of PA. Other microbial hosts suitable for use include bacilli, such as B. subtilus, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, if desired, the carboxy-terminal or other region of the antigen can be removed using standard oligonucleotide mutagenesis procedures.

The nucleotide (DNA) sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Host bacterial cells may be chosen that are mutated to be reduced in or free of proteases, so that the proteins produced are not degraded. For bacillus expression systems in which the proteins are secreted into the culture medium, strains are available that are deficient in secreted proteases.

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Fermentation and Purification Procedures

This invention relates to improved methods of preparing B. anthracis PA for use in vaccines. Procedures are exemplified herein for purifying modified PA from is a protease-deficient nonsporogenic avirulent strain of B. anthracis. However, it is expected that these procedures will be useful for growing and purifying PA, including natural or recombinant PA, as well as various modified or truncated forms of PA, from other microorganisms, particularly Bacillus. Bacillus strains and/or expression systems which are expected to be suitable include, for example, the B. anthracis strain described in U.S. Pat. No. 5,840,312 (Nov. 24, 1998) and the B. subtilis strain and PA expression system described in U.S. Pat. No. 6,267,966 (Jul. 31, 2001).

In the method of the invention, the culture is preferably maintained at about pH 7 to about pH 8, most preferably about pH 7.5, substantially throughout the fermentation process. It has also been found to be advantageous to add EDTA before separating the culture supernatant from the cells, preferably at or near the end of fermentation, since if it is added during the fermentation stage, it may interfere somewhat with the growth of the cells.

The purification procedure of the invention is preferably essentially a three-step procedure, including (1) hydrophobic interaction chromatography, (2) ion exchange chromatography and (3) gel filtration. While ion exchange chromatography may precede hydrophobic interaction chromatography in the purification process, and still permit obtaining a good yield of PA, it is a less efficient process. Therefore, in view of this, it is preferred that hydrophobic interaction chromatography precede ion exchange chromatography in the purification process. Alternatively, this three step procedure need not be used and an alternative purification scheme may be used.

In addition, the resins used in the exemplified the purification procedure can be substituted. For example, in the hydrophobic interaction chromatography step, phenyl sepharose (Pharmacia) is used as the resin in the example, but any other hydrophobic resin can be used. Likewise, in the ion exchange chromatography step, Q sepharose (Pharmacia) is used as the resin in the example, but any other anion exchanger can be used. Likewise, for the gel filtration step, Superdex (Pharmacia) is the residue used in the example, but it can be replaced by other gel filtration resins. Furthermore, with respect to the fermentation conditions, similar compounds can replace the tryptone and the yeast extract that are obtained from Difco.

The expression and the stability of two recombinant PA variants, PA-SNKE-ΔFF-E308D and PA-N657A, were studied. However, the methods of the invention are also expected to be useful for producing and recovering native PA; PA wherein the receptor-binding domain has been altered; PA which cannot be cleaved at the chymotrypsin cleavage site;

PA which cannot be cleaved at the furin cleavage site; other PA which cannot be cleaved at either the chymotrypsin or the furin cleavage site in addition to the one exemplified herein (see, e.g., those described in (22)); PA fragments (e.g., a PA fragment having aa 175-764 (36)); PA mutants having a strong dominant-negative effect (e.g., PA double mutants K397D and D425K) (37), and PA mutants with substitutions in domain 2 (37)).

In addition, the methods of the invention are also expected to be useful for producing and recovering PA in which the chymotrypsin site, FF, is replaced by a furin site. This may be a suicide protein, getting easily cleaved by furin after binding to receptor. Cleavage at that site inactivates PA.

The methods of the invention are also expected to be useful for producing and recovering PA with a protease cleavage site (thrombin, Factor IV, etc.) at approximately residue 605. PA made in large amounts in the expression system could be cleaved to produce a soluble domain 4, which would compete with PA for receptor, and could be a therapeutic agent.

The methods of the invention are also expected to be useful for producing and recovering PA with matrix metalloprotease or plasminogen activator sites replacing the furin site (38, 39).

The methods of the invention are also expected to be useful for producing and recovering other proteins, such as LF. See, e.g., (21), wherein expression system is the same, except the structural gene for PA is replaced by the LF gene. This can be generalized to include LF mutants altered in the catalytic site residues: HEFGH, 686-690. The system may also have utility with EF.

The following examples are exemplary of the present processes and incorporate suitable process parameters for use herein. These parameters may be varied, however, and the following should not be deemed limiting.

EXAMPLE 1

In this example, the expression and the stability of two recombinant PA variants, PA-SNKE-ΔFF-E308D and PA-N657A, were studied. These proteins were expressed in the non-sporogenic avirulent strain BH445. Initial results indicated that PA-SNKE-ΔFF-E308D, which lacks two proteolysis-sensitive sites, is more stable than PA-N657A. Process development was conducted to establish an efficient production and purification process for PA-SNKE-ΔFF-E308D. Various parameters such as pH, media composition, growth strategy, and protease inhibitors composition were analyzed. The production process chosen was based on batch growth of B. anthracis using tryptone and yeast extract as the only sources of carbon, pH control at 7.5, and antifoam 289. Optimal harvest time was found to be 14-18 hours after inoculation, and EDTA (5 mM) was added upon harvesting for proteolysis control. In one of the processes described herein, recovery of the PA was performed by expanded bed adsorption (EBA) on a hydrophobic interaction resin, eliminating the need for centrifugation, microfiltration, and diafiltration. The EBA step was followed by ion exchange and gel filtration. PA yields before and after purification were 130 mg/L and 90 mg/L, respectively.

Materials and Methods

Strains and Plasmids

The non-sporogenic, protease deficient, avirulent strain B. anthracis BH445 (pXO1[31], pXO2−, cm') was used (17). The Bacillus-E. coli shuttle vector pYS5 (amp', kan') (26) was used to clone two recombinant forms of the protective antigen: N657A and SNKE-.DELTA.FF- E308D (28). In the N657A mutant, the receptor-binding domain of PA was altered by substitution of Asp with Ala at position 657 (domain 4). In the SNKE-.DELTA.FF-E308D mutant two regions were altered, the furin site (RKKR[167] [SEQ ID NO: 14] to SNKE[167] [SEQ ID NO: 15]) and the chymotrypsin site (two Phe at positions 313-314 were deleted and Glu acid at position 308 was substituted with Asp). Both PA constructs contain the DNA sequence encoding the signal peptide of PA.

Culture and Expression Conditions

Modified FA medium (21) containing (per liter) 35 g tryptone (Difco Laboratories, Detroit, Mich.), 5 g yeast extract (Difco Laboratories), and 100 mL of 10× salts was used in all experiments. The 10× salt solution (per liter) consisted of 60 g Na$_2$HPO$_4$. 7H2O, 10 g KH$_2$PO$_4$, 55 g NaCl, 0.4 g L-tryptophan, 0.4 g L-methionine, 0.05 g thiamine, and 0.25 g uracil. It was filter-sterilized and added to the fermentor after cooling. The pH of the medium was adjusted to 7.5; 100 µg/mL kanamycin and 20 µg/mL chloramphenicol were added. Fermentation experiments were performed by inoculating a 12-14 hour-old starter culture grown from a frozen stock. The medium in the fermentor was supplemented with 0.2 mL /L of antifoam 289 (Sigma, St. Louis, Mo.). Three- to ten-liter fermentations were done using B. Braun Biostat MD DCU (Melsungen, Germany), controlling dissolved oxygen (DO) at 30% saturation, temperature at 37° C., and pH at 7.5 with HCl and NH$_4$OH. At harvest time, 5 mM EDTA and 10 µg/mL PMSF (phenylmethyl sulfonyl fluoride) (in one of the experiments described herein) were added to the culture. Shake flask experiments (100 mL) utilizing modified FA medium were supplemented with glucose, lactose, glycerol, and casitone at a concentration of 10 g/L.

Analytical Methods

Optical density (OD) was measured at 600 nm. Protease analysis was done on supernatant samples collected during growth and stored frozen at −20° C. EDTA was added to supernatant samples used for SDS-PAGE and radial immunodiffusion to a final concentration of 10 mM.

Extracellular protease activity was detected using the EnzChek green fluorescence assay kit (Molecular Probes Eugene, OR). Fluorescence was measured with a LS50B luminescence spectrophotometer (Perkin-Elmer Boston, Mass.). This assay was conducted at pH of 7.5 or 6.0 depending on the experiment. Proteolytic activity is reported as fluorescence change per unit sample.

Protein was determined using BCA assay (Pierce Rockford, Ill.). PA expression was quantified by SDS-PAGE (Invitrogen/Novex, Carlsbad, Calif.) gel analysis and by the Mancini immunodiffusion assay (19) using agarose plates containing polyclonal PA antibody. Pure PA was used as the standard, both polycolonal PA antibodies and pure PA were supplied by S. Leppla Purification a. Packed Bed Hydrophobic Interaction Chromatography The cell suspension containing 5 mM EDTA was centrifuged and the supernatant passed through a 0.2 µm hollow fiber filter (AGT, Needham, Mass.). The filtered broth was then concentrated 20× using a 10K membrane in a Pellicon-2 (Millipore, Bedford, Mass.). 200 g (NH$_4$)$_2$SO$_4$ per liter (1.5 M) were added to the concentrated supernatant. The small amount of precipitate produced after addition of (NH$_4$)$_2$SO$_4$ was eliminated with centrifugation and filtration. Phenyl Sepharose Fast Flow (Amersham Pharmacia Biotech) was equilibrated with buffer containing 1.5 M (NH$_4$)$_2$SO$_4$/10 mM HEPES/5 mM EDTA pH=7.0 (equilibration buffer) at a flow rate of 15 cm/h. After sample loading, the column was washed with 10 column volumes (CV) of equilibration buffer and PA was eluted with a 30 CV linear gradient from 1.5 M to 0 M (NH$_4$)$_2$SO$_4$ in 10 mM HEPES/5 mM EDTA; pH=7.0. Fractions were analyzed by SDS-PAGE and the PA-containing samples were pooled for further purification.

b. Expanded Bed Hydrophobic Interaction Chromatography

The cell suspension containing 5 mM EDTA was diluted 1:1 with buffer containing 3.0 M (NH$_4$)$_2$SO$_4$/20 mM HEPES/5 mM EDTA and 0.005% Pluronic F-68 (Life Technologies, Inc. Gaithersburg, MD). STREAMLIN™ Phenyl adsorbent, (Amersham Pharmacia Biotech) was expanded in a streamline column in equilibration buffer. The diluted cell suspension was loaded upward at 300 cm/h. The column was washed in expanded mode (2) with 10 CV of equilibration buffer containing 0.005% pluronic F-68. Elution was performed in packed bed mode with 8 CV of elution buffer at 100 cm/h. The eluent was analyzed by SDS-PAGE and radial immunodifussion.

c. Anion Exchange Chromatography

Fractions from HIC were dialyzed against 20 mM Tris pH=8.9 and loaded on a Q Sepharose Fast Flow (Amersham Pharmacia Biotech) column equilibrated with 20 mM Tris pH=8.9 at 15 cm/h. The protein was eluted using a 20 CV linear gradient from 0 to 0.5 M NaCl in the same buffer. PA containing fractions were concentrated and dialyzed against PBS.

d. Gel Filtration

The pooled PA was further purified using a Superdex 75 column (Amersham Pharmacia Biotech) in PBS/5 mM EDTA pH=7.4 at 12 cm/h.

Results and Discussion a. Expression of Two Recombinant PA: PA-N657A and PA-SNKE-ΔFF-E308D The expression of two recombinant versions of PA and the extracellular proteolytic activity of the culture were analyzed (FIG. 1). Production of PA-SNKE-ΔFF-E308D, the protein lacking the furin and chymotrypsin cleavage sites, was nearly 60% higher than that of PA-N657A, the protein containing a mutation in the receptor-binding domain (FIG. 1a). The extracellular proteolytic activity (fluorescence/OD) of both cultures was similar. SDS-PAGE analysis of partially purified PA recovered from these cultures shows higher concentration of smaller fragments in the sample from PA-N657A compared to the sample from PA-SNKE-ΔFF-E308D (FIG. 1b). Western blot analysis with polyclonal PA antibody confirmed that the smaller fragments were reactive against PA (data not shown). As indicated in FIG. 1a, the proteolytic activity was similar in both strains. Therefore, it was apparent that PA-SNKE-ΔFF-E308D is a better candidate, due to its stability, and it was selected for further studies.

b. pH Effect

Based on previous information (5, 21), initial production studies with PA-SNKE-ΔFF-E308D were done by controlling pH with NH$_4$OH only, which resulted in pH 8.7 at the end of the fermentation. When pH was controlled at 7.4 during the entire fermentation, the PA production was 30 mg per g cell and the proteolytic activity per OD unit was 8, compared to values of 20 mg PA per g cells and proteolytic activity per OD of 30 when the pH control was done only by NH$_4$OH. When the process was performed at a lower pH, both PA production and protease activity were lower. At pH 6.1 production declined nearly six times and protease activity two times compared to what was found at pH 7.4. Possibly, intracellular expression is lower or secretion is inhibited at low pH. From the above information it is obvious that pH significantly affects the proteolytic activity and the PA expression. Controlling pH throughout the fermentation process resulted in a 30% increase in PA yield, compared to previously reported strategies.

c. Effect of Various Carbon Sources and Protease Inhibitors

Attempts to increase PA expression by supplementing the basic growth medium with different carbon sources is summarized in Table 1.

TABLE 1

Effect of various carbon sources on PA production.

| Medium | PA production | |
|---|---|---|
| | mg PA/g cell | mg PA/L culture |
| Basic medium | 31.3 | 129.5 |
| Glycerol + basic medium | 23.7 | 117.3 |
| Glucose + basic medium | 25.3 | 113.3 |
| Lactose + basic medium | 33.9 | 116.0 |
| Casitone + basic medium | 28.3 | 135.1 |

Neither the volumetric production nor the production per gram cells could be enhanced with the addition of various carbon sources. The effect of PMSF and EDTA on extracellular proteolysis was also examined. As shown in FIG. 2, addition of EDTA (15 mM) significantly reduced proteolytic activity whereas the proteolytic activity of the PMSF-containing fraction (1 g/mL) was similar to that of the control. Based on this information, EDTA was added at the end of the fermentation, before the protein was processed.

d. Growth and Production Conditions

Based on the parameters determined previously, a production process for the recombinant PA-SNKE-ΔFF-E308D from B. anthracis BH445 was established. The process is based on growth in a batch fermentation controlled at pH 7.5 with NH$_4$OH/HCl and at 30% dissolved oxygen saturation for a period of 18 hours. A typical fermentation is seen in FIG. 3.

Figure 4:
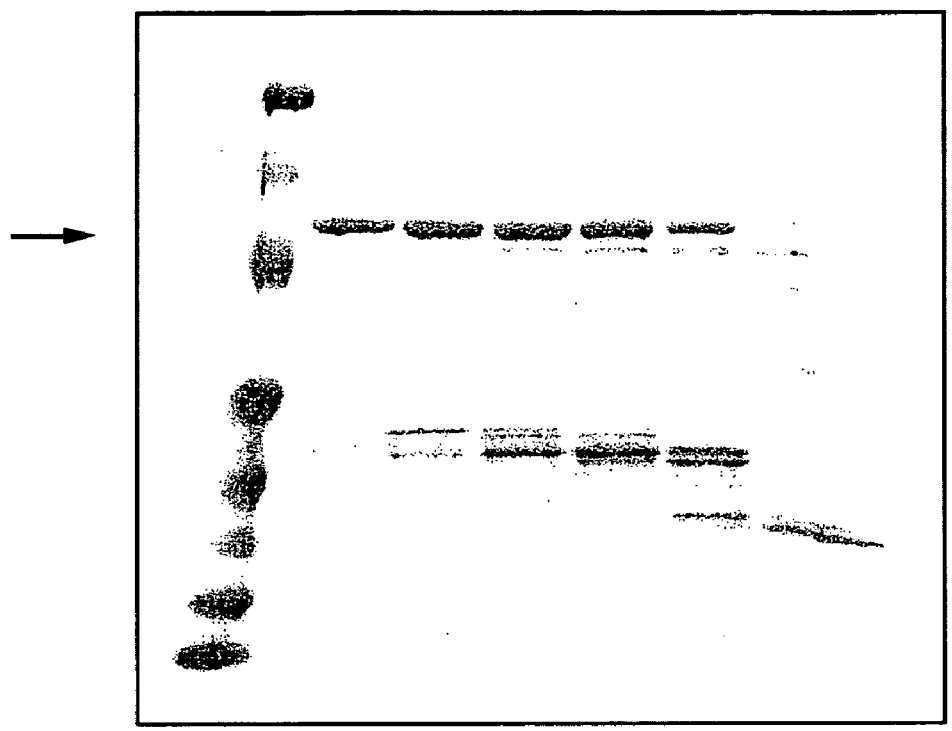
FIG. 4. SDS-PAGE analysis of culture supernatants obtained throughout the fermentation. Samples were taken at 13, 14, 16, 18, 22, and 34 hours of growth. Arrow indicates the location of PA(83 KDa) in the gel.

In general, the final OD$_{600}$ values fluctuated between 16 to 20. During the first five hours, growth was exponential and the pH was controlled by base addition. Later in the fermentation the pH was controlled by acid addition. Accumulation of PA occurred mostly during the stationary phase and reached a final concentration of 160 mg per liter. The results shown in FIG. 4 indicate that PA degraded if the fermentation was extended for more than 18 hours, therefore, a harvest time between 14 and 18 hours was selected.

Figure 6:
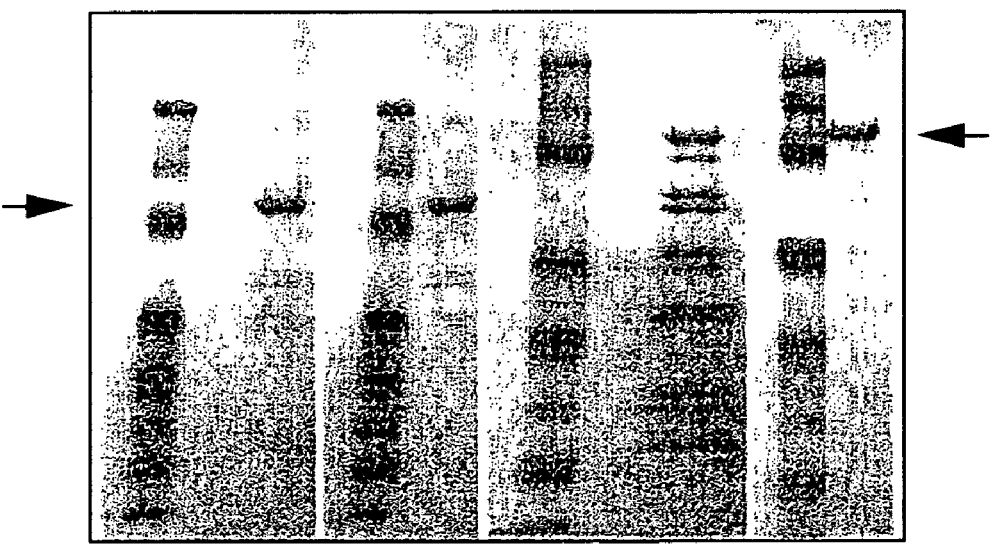
FIG. 6. SDS-PAGE analysis of purified PA fractions. (a) PA purified by packed bed chromatography; (b) PA after hydrophobic interaction chromatography and gel filtration; (c) PA fraction shown in Lane (b) after 3 months; (d) PA after expanded bed hydrophobic interaction chromatography, anion exchange, and gel filtration. MW indicates molecular weight markers. Arrows indicate the location of PA(83 KDa) in the gel.
Figure 5:
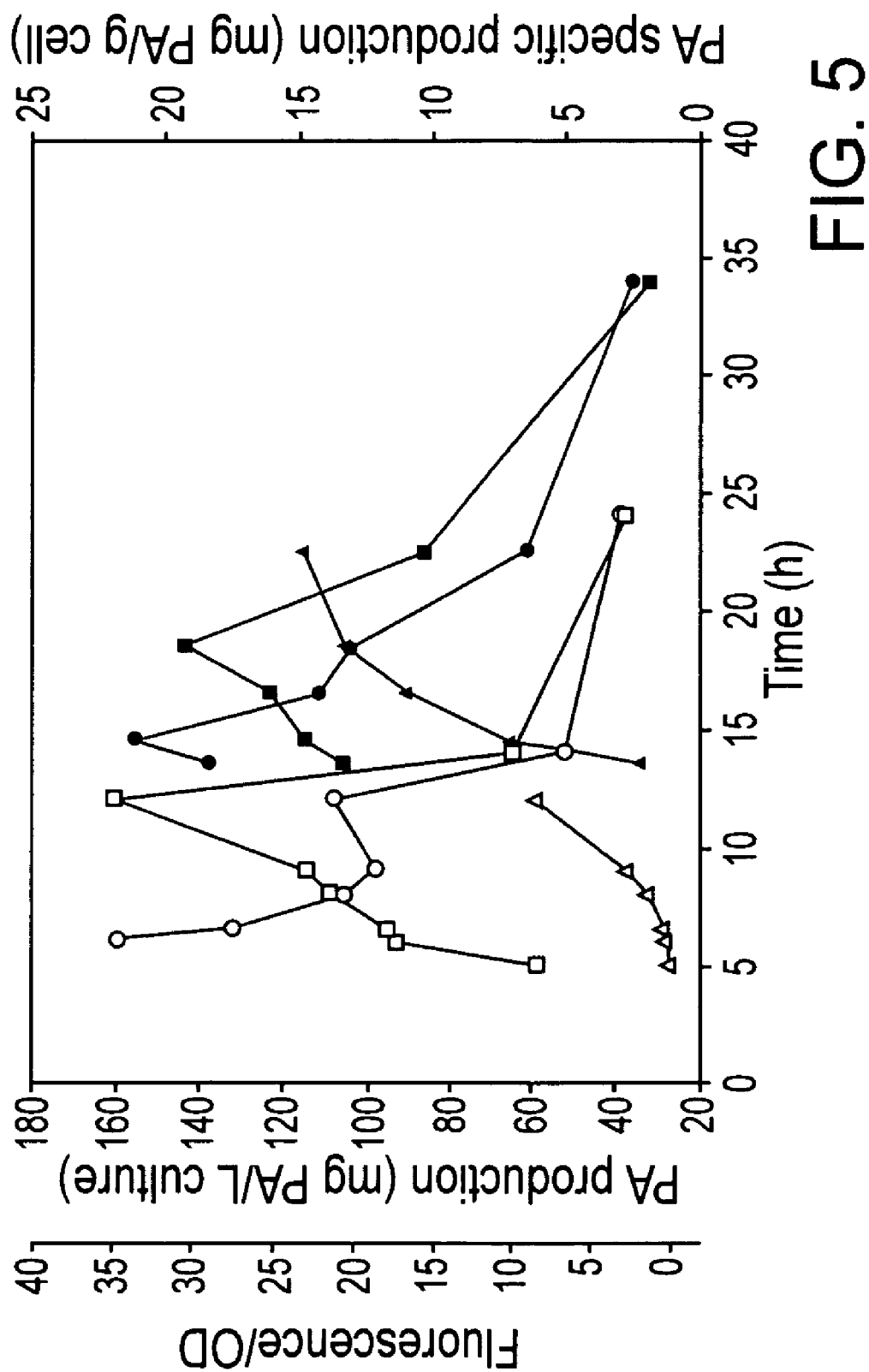
FIG. 5. PA production and proteolytic activity of *B. anthracis* BH445 [pSY5:SNKE-ΔFF-E308D] in fed-batch cultures supplied with tryptone/yeast extract or glucose. ● Specific PA production in tryptone/yeast extract (mg/g cells); ■ Volumetric PA production in tryptone/yeast extract (mg/liter); ▲ Proteolytic activity in tryptone/yeast extract; ○ Specific PA production in glucose (mg/g cells); □ Volumetric PA production in glucose (mg/liter); Δ Proteolytic activity in glucose.

Attempts to increase the PA production by implementing a fed-batch growth strategy were conducted. The addition of 10× tryptone/yeast extract/salts or 50% glucose/10× salts resulted in a 50% increase in cell density but not an increase in protein production (FIG. 5). The observations that PA production was not improved by the implementation of a fed batch growth strategy or by the addition of various carbon sources such as casein, glucose, glycerol or lactose is an indication that perhaps a specific nutritional factor is missing. It is also important to mention that the specific proteolytic activity was almost five times lower when glucose was added to the tryptone/yeast extract media (FIG. 6). This was expected since glucose is known to be a repressor of proteases in Bacillus (10, 25).

e. Purification

The purification protocol developed for PA (Materials and Methods) consisted of hydrophobic interaction chromatography (Phenyl Sepharose) followed by anion exchange (Q Sepharose) and gel filtration (Superdex 75).

Replacing the initial capturing step with expanded bed chromatography (2) can simplify and shorten the recovery process since it eliminates the clarification steps. Therefore, the use of expanded bed adsorption (EBA) was investigated by substituting the traditional packed-bed resin (Phenyl Sepharose) with the expanded bed hydrophobic resin STREAMLIN™ Phenyl adsorbent. The static binding capacity for STREAMLIN™ Phenyl adsorbent was approximately 15 mg protein/mL of resin which is comparable to the capacity of Phenyl Sepharose. Optimal binding of PA to S STREAMLIN™ Phenyl adsorbent occurred at 1.5 M $(NH_4)_2SO_4$.

Preliminary experiments performed with cell-containing broth in expanded mode resulted in the formation of aggregates and eventual collapse of the bed. It was possible to stabilize the expanded column only after the addition of a detergent which probably altered some of the hydrophobic interactions but did not prevent PA from binding. Pluronic F-68 was chosen due its non-toxicity in humans. The static binding capacities of STREAMLIN™ Phenyl adsorbent were 15, 11, and 5 mg protein/mL resin with 0%, 0.005%, and 0.01% pluronic F-68, respectively. Successful operation of the HIC EBA column occurred when using a load concentration of 15 g wet cells/L, 0.8 mL resin/g wet cells, and 0.005% pluronic F-68 in the load as well as the wash buffer. Under these conditions some signs of aggregation appeared at the end of the loading phase but cell debris was eliminated in the washing phase. A 70% recovery was obtained.

PA purity after hydrophobic interaction chromatography was higher than 80%. Further purification was achieved by adding gel filtration step (FIG. 6, Lane b). However, this material was not stable when stored at 4□ C. for three months (FIG. 6, Lane c). In contrast, pure and stable PA was obtained after hydrophobic interaction chromatography on expanded bed, followed by anion exchange and gel filtration (FIG. 6, Lane d ). Similar results to the expanded bed process were obtained when packed bed hydrophobic interaction chromatography was followed by ion exchange and gel filtration (FIG. 6, Lane a).

Replacing the packed-bed capturing step with expanded bed adsorption proved to be more efficient since it eliminated the centrifugation and filtration steps, however, twenty times more $(NH_4)_2SO_4$ and three times more resin were required to process the same amount of culture (Table 2).

TABLE 2

Comparison of packed bed and expanded bed absorption as capturing processes for PA

| Packed Bed | Expanded Bed Adsorption |
|---|---|
| 1. Total processing time 15.5 h | 1. Total processing time: 8 h |
| a) downstream processing: 6 h | a) downstream processing: 1 h |
| (4 unit operations) | (1 unit operation) |
| b) loading: 2 h | b) loading: 4 h |
| c) column wash: 3.5 h | c) column wash: 1.5 h |
| d) elution: 4 h | d) elution: 1.5 h |
| 2. 400 g $(NH_4)_2SO_4$ needed | 2. 8000 g $(NH_4)_2SO_4$ needed |
| 3. 100 mL resin needed | 3. 300 mL resin needed |
| 4. Load/wash steps require little attention | 4. Load/wash steps cannot be left unattended |
| 5. 82% recovery | 5. 70% recovery |

Initial work with hydrophobic interaction chromatography using expanded bed ad sorption to capture PA resulted in bed collapse. This was avoided after the addition of a surfactant (pluronic F-68). These results suggest that the characteristics of the cell membrane were most likely the cause of cell aggregation. Since no polyglutamic acid capsule is present in the recombinant strain, the two hydrophobic membrane proteins forming the S-layer (4, 6) may be responsible for associating with neighboring cell membranes and the resin. After evaluating the possible interactions affecting the system, it was found that successful operation of the expanded bed was possible by carefully adjusting the cell concentration of the load, increasing the adsorbent-to-cell ratio, and choosing the appropriate detergent type and concentration. The expanded bed approach was more efficient in spite of the slightly lower yield (70% vs. 82%) and the higher amount of $(NH_4)_2SO_4$ and resin needed since it eliminated the need for centrifugation and filtration. To obtain stable and highly purified protein, anion exchange and gel filtration steps were added.

Conclusions

Once the gene encoding PA (pagA) was cloned (31) and sequenced (32), several researchers have reported on the expression of PA in hosts like *B. subtilis* (1, 13, 20, 26), *E. coli* (8, 24, 31), *Salmonella typhimurium* (3), viruses (11), and avirulant *B. anthracis* (5, 15). From these reports, the highest PA yield achieved has been in the order of 50 mg/L in *B. anthracis* (15). In this work, a scalable fermentation and purification process suitable for vaccine development which produced almost three times more product than what have been reported earlier, is presented. This was accomplished by using a biologically inactive protease-resistant PA variant in a protease-deficient nonsporogenic avirulent strain of *B. anthracis*.

EXAMPLE 2

Composition of the Vaccines

Four combinations of the recombinant (modified) protective antigen ("rPA") were made: (1) rPA in PBS ("phosphate buffered saline"), (2) rPA in formalin, (3) rPA in aluminum hydroxide and (4) rPA in formalin and aluminum hydroxide. Another formulation of succinylated rPA was prepared and tested (data not shown).

EXAMPLE 3

Immunogenicity in Mice

The four formulations described above were immunogenic in mice, and induced antibody levels comparable to those induced by the currently licensed anthrax vaccine. The induced antibodies had anthrax toxin neutralizing activity. It is planned to evaluate these formulations in humans, and to chose the best one for use as a vaccine.

The data from the mice experiments are set forth in the tables 3 to 5 below:

TABLE 3

Number of Mice and Immunogen

| Group Number | Number of Mice | Immunogen |
|---|---|---|
| 1056 | 11 | PA (2.5 μg)-Untreated |
| 1057 | 11 | PA (12.5 μg)-Untreated |
| 1058 | 11 | PA (2.5 μg) + Alum |
| 1059 | 10 | $PA_{SUCC}$ 10:1.25 (2.5 μg) |
| 1060 | 10 | $PA_{SUCC}$ 10:1.25 (12.5 μg) |
| 1061 | 10 | $PA_{SUCC}$ 10:3 (2.5 μg) |
| 1062 | 10 | $PA_{SUCC}$ 10:3 (12.5 μg) |
| 1063 | 10 | PA-Formalin 0.3 (2.5 μg) |
| 1064 | 10 | PA-Formalin 0.3 (12.5 μg) |
| 1065 | 10 | PA-Formalin 3.0 (2.5 μg) |
| 1066 | 10 | PA-Formalin 3.0 (12.5 μg) |

TABLE 3-continued

Number of Mice and Immunogen

| Group Number | Number of Mice | Immunogen |
|---|---|---|
| 1067 | 10 | PA-Formalin 7.12 (2.5 μg) |
| 1068 | 10 | PA-Formalin 7.12 (12.5 μg) |
| 1069 | 11 | Anthrax Vaccine 0.1 ml |
| 1070 | 10 | Control |

TABLE 4

Antibody Levels and Neutralization Titers

| Mice | μg/ml | Neutral, Titer |
|---|---|---|
| 1056A | 130.64 | 4000 |
| 1056B | 11.24 | 200 |
| 1056K | 21.3 | 1000 |
| 1057A | 146.65 | 3000 |
| 1057I | 490.14 | 7000 |
| 1058A | 725.31 | 8000 |
| E | 710.46 | 7000 |
| J | 513.46 | 4000 |
| 1059A | 53.89 | 1500 |
| 1060A | 125.92 | 850 |
| 1061A | 97.1 | 1500 |
| C | 21.2 | 200 |
| E | 54.22 | 700 |
| 1062A | 24.9 | 1500 |
| J | 14.35 | 2000 |
| 1063A | 68.31 | 1500 |
| C | 179.16 | 2000 |
| H | 564.94 | 2000 |
| 1064A | 581.34 | 10,000 |
| 1064D | 204.56 | 8000 |
| E | 742.21 | 11,000 |
| F | 418.95 | 7000 |
| G | 814.91 | 10,000 |
| 1065A | 77.73 | 1250 |
| E | 214.37 | 5000 |
| 1066C | 65.47 | 4000 |
| D | 513.32 | 10,000 |
| E | 248.91 | 4000 |
| F | 260.36 | 8000 |
| J | 1041.65 | 10,000 |
| 1067A | 261.54 | 3000 |
| G | 415 | 5000 |
| 1068A | 512.99 | 10,000 |
| I | 414.82 | 5000 |
| 1069A | 339.18 | 3000 |
| 1069J | 879.65 | 3000 |
| 1070E | <.05 | 20 |

5-6 weeks old female general purpose mice were injected subcutaneously with 0.1 mL of the immunogens depicted in Table 3, 2 or 3 times 2 weeks apart. The mice were exsanguinated one week after the last injection and their sera assayed for IgG anti PA and anthrax toxin neutralization. Antibodies measured by Elisa were related to a standard containing 1.8 mg/ml of anti-PA monoclonal antibody.

TABLE 5

IgG anti PA levels induced in mice by various rPA formulations

| PA lot | formulation | dose × number of injections | μg/ml |
|---|---|---|---|
| 0 | PA | 2.5 μ × 2 | 1.3 |
| 0 | PA | 2.5 μ × 3 | 109.1 |
| 2 | PA | 2.5 μ × 3 | 24.9 |
| 2 | PA | 12.5 μ × 3 | 226 |
| 0 | PA/Al (OH)₃ | 2.5 μ × 2 | 86.1 |
| 0 | PA/Al (OH)₃ | 2.5 μ × 3 | 312. |
| 2 | PA/Al (OH)₃ | 2.5 μ × 3 | 435. |
| 2 | PA formalin 0.3 | 2.5 μ × 3 | 182 |
| 2 | PA formalin 0.3 | 12.5 μ × 3 | 350. |
| 0 | PA formalin 3.0 | 2.5 μ × 2 | 2.79 |
| 0 | PA formalin 3.0 | 2.5 μ × 3 | 136.4 |
| 0 | PA formalin 3.0 | 5.0 μ × 2 | 1.98 |
| 2 | PA formalin 3.0 | 2.5 μ × 3 | 220 |
| 2 | PA formalin 3.0 | 12.5 μ × 3 | 270 |
| 0 | PA formalin 7.12 | 2.5 μ × 3 | 266 |
| 0 | PA formalin 7.12 | 12.5 μ × 3 | 229 |
| Anthrax Vaccine | | 1/10 human dose × 2 | 43.15 |
| | | 1/10 human dose × 3 | 297 |
| PBS control | | × 2 | <.05 |
| | | × 3 | <.05 |

5-6 weeks old female mice, 10 per group, were injected subcutaneously with the listed formulations, 2 or 3 times, two weeks apart and exsanguinated one week after the last injection. Antibodies were measured by Elisa, calculated relative to a standard containing 1.8 mg/ml of anti-PA monoclonal antibody, and expressed as geometric means of the groups.

REFERENCES

1. Baillie L, A Moir and R Manchee. 1998. The expression of the protective antigen of *Bacillus anthracis* in *Bacillus subtilis*. J. Appl. Microbiol. 84, 741-746.

2. Chase H A. 1994. Purification of proteins by adsorption chromatography in expanded bed. Trends Biotechnol. 12, 296-303.

3. Coulson N M, M Fulop and R W Titball. 1994. *Bacillus anthracis* protective antigen expressed in *Salmonella typhimurium* SL3261 affords protection against anthrax spore challenge. Vaccine 12, 1395-1401.

4. Farchaus J W, W J Ribot, M B Downs and J W Ezzell. 1995. Purification and characterization of the major surface array protein from the avirulent *Bacillus anthracis* Δ Sterne-1. J. Bacteriol. 177, 2481-2489.

5. Farchaus J W, W J Ribot, S Jendrek and S F Little. 1998. Fermentation, purification, and characterization of protective antigen from a recombinant, avirulent strain of *Bacillus anthracis*. Appl. Environ. Microbiol. 64, 982-991.

6. Fouet A, S Mesnage, E Tosi-Couture, P Gounon and M Mock. 1999. *Bacillus anthracis* surface: capsule and S-layer. J. Appl. Microbiol. 87, 251-255.

7. Gladstone G P. 1946. Immunity to anthrax: protective antigen present in cell-free culture filtrates. Br. J. Exp. Pathol. 27, 394-418.

8. Gupta P, S M Waheed and R Bhatnagar. 1999. Expression and purification of the recombinant protective antigen of *Bacillus anthracis*. Protein Expr. Purif. 16, 369-376.

9. Hambleton P and P C B Turnbull. 1990. Anthrax vaccine development: a continuing story. Adv. in Biotechnol. Processes 13, 105-122.

10. Hemila H, M Pokkinen and I Palva. 1992. Improving the production of *E. coli* β-lactamase in Bacillus subtilis: the effect of glucose, pH, and temperature on the production level. J. Biotechnol. 26, 245-256.

11. Iacono-Connors L C, C S Schmaljohn and J M Dalrymple. 1990. Expression of the *Bacillus anthracis* protective antigen gene by baculovirus and vaccinia virus recombinants. Infect. Immun. 58, 366-372.

12. Ivins B E, M L M Pitt, P F Fellows, J W Farchaus, G E Benner, D M Waag, S F Little, G W Anderson, P H Gibbs and A M Friedlander. 1998. Comparative efficacy of experimental anthrax vaccine candidates against inhalation anthrax in rhesus macaques. Vaccine 16, 1141-1148.

13. Ivins B E and S L Welkos. 1986. Cloning and expression of the *Bacillus anthracis* protective antigen gene in *Bacillus subtilis*. Infect. Immun. 54, 537-542.

14. Keppie J, P W Harris-Smith and H Smith. 1963. The chemical basis of the virulence of *Bacillus anthracis*. IX. Its aggressins and their mode of action. Br. J. Exp. Pathol. 44, 446-453.

15. Leppla S H. 1988. Production and purification of anthrax toxin. Methods Enzymol. 165, 103-116.

16. Leppla S H. 1991. The anthrax toxin complex. In: Sourcebook of bacterial toxins, (Alouf, J. E. and Freer, J. H., eds) pp. 277-302. Academic Press, Inc. San Diego, Calif.

17. Leppla S H. 1995. Anthrax toxins. In: Bacterial toxins and virulence factors in disease. Handbook of natural toxins, (Moss, J., Iglewski, B., Vaughan, M., and Tu, A., eds) pp. 543-572. Dekker N.Y.

18. Little S F, B E Ivins, P F Fellows and A M Friedlander. 1997. Passive protection by polyclonal antibodies against *Bacillus anthracis* infection in guinea pigs. Infect. Immun. 65, 5171-5175.

19. Mancini G, A O Carbonara and J F Hermans. 1966. Immunological quantitation of antigens by single radial immunodiffusion. Immunochemistry 2, 235-354.

20. Miller J, B W McBride, R J Manchee, P Moore and L W Baillie. 1998. Production and purification of recombinant protective antigen and protective efficacy against *Bacillus anthracis*. Lett. Appl. Microbiol. 26, 56-60.

21. Park S and S H Leppla. 2000. Optimized production and purification of *Bacillus anthracis* lethal factor. Protein Expression and Purification 18, 293-302.

22. Puziss M, L C Manning, L W Lynch, E Barclay, I Abelow and G G Wright. 1963. Large-scale production of protective antigen of *Bacillus anthracis* anaerobic cultures. Appl. Microbiol. 11, 330-334.

23. Reuveny S, M D White, Y Y Adar, Y Kafri, Z Altboum, Y Gozes, D Kobiler, A Shafferman and B Velan. 2001. Search for correlates of protective immunity conferred by anthrax vaccine. Infect. Immun. 69, 2888-2893.

24. Sharma M, P K Swain, A P Chopra, V K Chaudhary and Y Singh. 1996. Expression and purification of anthrax toxin protective antigen from *Escherichia coli*. Protein Expr. Purif. 7, 33-38.

25. Simonen M and I Palva. 1993. Protein secretion in *Bacillus species*. Microbiol. Rev. 57,109-137.

26. Singh Y, V K Chaudhary and S H Leppla. 1989. A deleted variant of *Bacillus anthracis* protective antigen is non-toxic and blocks anthrax toxin action in vivo. J. Biol. Chem. 264, 19103-19107.

27. Singh Y, B E Ivins and S H Leppla. 1998. Study of immunization against anthrax with the purified recombinant protective antigen of *Bacillus anthracis*. Infect. Immun. 66, 3447-3448.

28. Singh Y, K R Klimpel, N Arora, M Sharma and S H Leppla. 1994. The chymotrypsin-sensitive site, FFD315, in anthrax toxin protective antigen is required for translocation of lethal factor. J. Biol. Chem. 269, 29039-29046.

29. Thorne C B. 1985. Genetics of *Bacillus anthracis*. In: Microbiology, (Leive, L., Bonventre, P. F., Morello, J. A., Schlesinger, S., Silver, S. D., and Wu, H. C., eds) pp. 56-62. American Society for Microbiology Washington, D.C.

30. Turnbull P C B. 1991. Anthrax vaccines: past, present, and future. Vaccine 9, 533-539.

31. Vodkin M H and SH Leppla. 1983. Cloning of the protective antigen gene of *Bacillus anthracis*. Cell 34, 693-97.

32. Welkos S L, J R Lowe, F Eden-McCutchan, M Vodkin, S H Leppla and J J Schmidt. 1988. Sequence and analysis of the DNA encoding protective antigen of *Bacillus anthracis*. Gene 69, 287-300.

33. Ezzell J W, Welkos SL. 1999. The capsule of bacillus anthracis, a review. J Appl Microbiol. 87(2), 250.

34. C. Chu, et al. 1991. Infect. Immun., 59:4450-4458.

35. Kossaczka, Z., Bystricky, S., Bryla, D. A., Shiloach, J., Robbins, J. B., and Szu, S. C. 1997. Synthesis and immmunological properties of Vi and di-o-acetyl pectin conjugates with adipic acid dihydrazide as the linker. Infect. Immun. 65:2088-2093.

36. Price B M, A L Liner, S Park, S H Leppla, A Mateczun, and D R Galloway. Protection against anthrax lethal toxin challenge by genetic immunization with a plasmid encoding the lethal factor protein. Infect. Immum. 69(7):4509-4515 (2001).

37. Leppla, S H. A dominant-negative therapy for anthrax. Nature Medicine 7(6):659-670 (June 2001).

38. Liu S, S Netzel-Arnett, H Birkedal-Hansen, and S H Leppla. Tumor cell-selective cytotoxicity of matrix metalloproteinase-activated anthrax toxin. Cancer Res. 2000 Nov 1;60(21):6061-7.

39. Liu S, T H Bugge, and S H Leppla. Targeting of tumor cells by cell surface urokinase plasminogen activator-dependent anthrax toxin. J Biol Chem. May 25,2001 ;276(21): 17976-84.

The disclosures of all the references cited hereinabove are incorporated by reference herein.

Modifications of the above described modes for carrying out the invention that are obvious to those of skill in the fields of immunology, protein chemistry, microbiology, medicine, and related fields are intended to be within the scope of the following claims.

We claim:

1. A method of producing a *Bacillus anthracis* protective antigen protein, comprising:
fermenting in a fermentation medium a cell or microorganism comprising a nucleotide sequence encoding said *B. anthracis* protective antigen protein in a manner to cause expression of said protective antigen, wherein the fermentation medium comprises dissolved oxygen at 30% saturation and is maintained at about pH 7 to about pH 8 throughout the fermenting.

2. The method of claim 1 further comprising recovering said protective antigen.

3. The method of claim 2 wherein said recovering step further comprises using hydrophobic interaction chromatography, ion exchange chromatography and gel filtration.

4. The method of claim 1 or 2 wherein the cell or microorganism is a protease-deficient nonsporogenic avirulent strain of *B. anthracis*.

5. The method of claim 1 wherein the *B. anthracis* protective antigen is a modified *B. anthracis* protective antigen wherein the receptor-binding domain has been altered.

6. The method of claim 5 wherein the *B. anthracis* protective antigen comprises an N657A substitution (SEQ ID NO: 5).

7. The method of claim 1 wherein the *B. anthracis* protective antigen is a modified *B. anthracis* protective antigen which cannot be cleaved at the chymotrypsin cleavage site.

8. The method of claim 7, wherein the modified protective antigen comprises an D315A substitution in SEQ ID NO: 3.

9. The method of claim 7, wherein the modified protective antigen comprises an F313A and an F314A substitution in SEQ ID NO: 3.

10. The method of claim 7, wherein the modified protective antigen comprises an F313C substitution in SEQ ID NO: 3.

11. The method of claim 1 wherein the *B. anthracis* protective antigen is a modified *B. anthracis* protective antigen which cannot be cleaved at the furin cleavage site.

12. The method of claim 11 wherein the *B. anthracis* protective antigen amino acid sequence RKKR$^{167}$ (SEQ ID NO: 14) in SEQ ID NO: 3 has been changed to SNKE$^{167}$ (SEQ ID NO: 15).

13. The method of claim 1 wherein the *B. anthracis* protective antigen is a modified *B. anthracis* protective antigen which cannot be cleaved at either the chymotrypsin or furin cleavage site.

14. The method of claim 13 wherein the amino acid sequence RKKR$^{167}$ (SEQ ID NO: 14) has been changed to SNKE$^{167}$ (SEQ ID NO: 15), the two phenylalanines at positions 313-314 are deleted and the glutamic acid at position 308 is substituted with aspartic acid.

15. The method of claim 2 wherein EDTA is added to the culture medium prior to the recovery step.

16. The method of claim 1, wherein the pH is maintained with HCl and NH$_4$OH.

17. The method of claim 1, wherein the pH is maintained at about pH 7.5 throughout the fermentation.

18. The method of claim 3, wherein the hydrophobic interaction chromatography precedes the ion exchange chromatography.

19. The method of claim 1, wherein the *B. anthracis* protective antigen sequence comprises SEQ ID NO: 3.

20. The method of claim 1, wherein the *B. anthracis* protective antigen sequence is a fragment of a *B. anthracis* protective antigen sequence comprising SEQ ID NO: 13, and wherein the fragment *B. anthracis* protective antigen sequence can produce an immune response in a mammal.

21. The method of claim 1, wherein the *B. anthracis* protective antigen sequence comprises any of SEQ ID NOS: 3-13.

22. The method of claim 14, wherein the *B. anthracis* protective antigen amino acid sequence comprises SEQ ID NO: 4.

23. The method of claim 5, wherein the *B. anthracis* protective antigen amino acid sequence comprises SEQ ID NO: 5.

24. The method of claim 4, wherein the protease-deficient nonsporogenic avirulent strain of *B. anthracis* is BH445 (pXO 1-, pXO2-).

25. A method of producing a *Bacillus anthracis* exotoxin protein comprising fermenting in a fermentation medium a cell or microorganism comprising a nucleotide sequence encoding said *B. anthracis* exotoxin protein in a manner to cause expression of exotoxin protein wherein the-fermentation medium comprises dissolved oxygen at 30% saturation and is maintained at about pH 7 to about pH 8 throughout the fermenting.

26. The method of claim 25, wherein the exotoxin protein is a *Bacillus anthracis* lethal factor or protective antigen.

27. The method of claim 26, wherein the exotoxin protein is a *Bacillus anthracis* lethal factor.

28. The method of claim 27, further comprising recovering said lethal factor.

29. The method of claim 27, wherein the *B. anthracis* lethal factor is a modified *B. anthracis* lethal factor wherein a catalytic site of the lethal factor has been altered.

30. The method of claim 25, wherein the pH is maintained with HCl and NH$_4$OH.

* * * * *